United States Patent [19]

Asano et al.

[11] Patent Number: 5,824,534
[45] Date of Patent: Oct. 20, 1998

[54] AMINOPEPTIDASE GX, AND A METHOD OF HYDROLYZING A PROTEIN WITH THE SAME

[75] Inventors: Minao Asano; Misako Kawai; Tetsuya Miwa; Noriki Nio, all of Kawasaki, Japan

[73] Assignee: Ajinomoto Co., Inc., Tokyo, Japan

[21] Appl. No.: 813,591

[22] Filed: Mar. 7, 1997

[30] Foreign Application Priority Data

Mar. 8, 1996 [JP] Japan ..................................... 8-051848
Feb. 14, 1997 [JP] Japan ..................................... 9-030458

[51] Int. Cl.$^6$ .............................. C12N 9/48; C12P 13/04; C12P 13/20; C12P 13/14
[52] U.S. Cl. .......................... 435/212; 435/106; 435/109; 435/110; 435/68.1
[58] Field of Search ................................... 435/212, 68.1, 435/106, 109, 110

[56] References Cited

PUBLICATIONS

Papastoitsis G and Wilson K, Initiation of the degradation of the soybean Kunitz and Bowman–Birk trypsin inhibitors by a cysteine protease, Plant Physiology 96: 1086–1092, 1991.

Couton J, Sarath G and Wagner F, Purification and characterization of a soybean cotyledon aminopeptidase, Plant Science 75: 9–17, 1991.

Kiang Y, Gorman M and Chiang Y, Genetic and linkage analysis of a leucine aminopeptidase in wild and cultivated soybean, Crop Science 25:319–321, 1985.

*Primary Examiner*—Eric Grimes
*Assistant Examiner*—Peter P. Tung
*Attorney, Agent, or Firm*—Oblon, Spivak, McClelland, Maier & Neustadt, P.C.

[57] ABSTRACT

An aminopeptidase is provided which efficiently decomposes a low-molecular-weight peptide containing glutamic acid or aspartic acid in its sequence. A method of hydrolyzing a peptide or protein by use of the aminopeptidase is also provided. Aminopeptidase GX is derived from germinated soybean cotyledons and releases glutamic acid or aspartic acid from a peptide or protein containing glutamic acid or aspartic acid at the N-terminal end and is used to hydrolyse peptides or proteins.

5 Claims, 13 Drawing Sheets

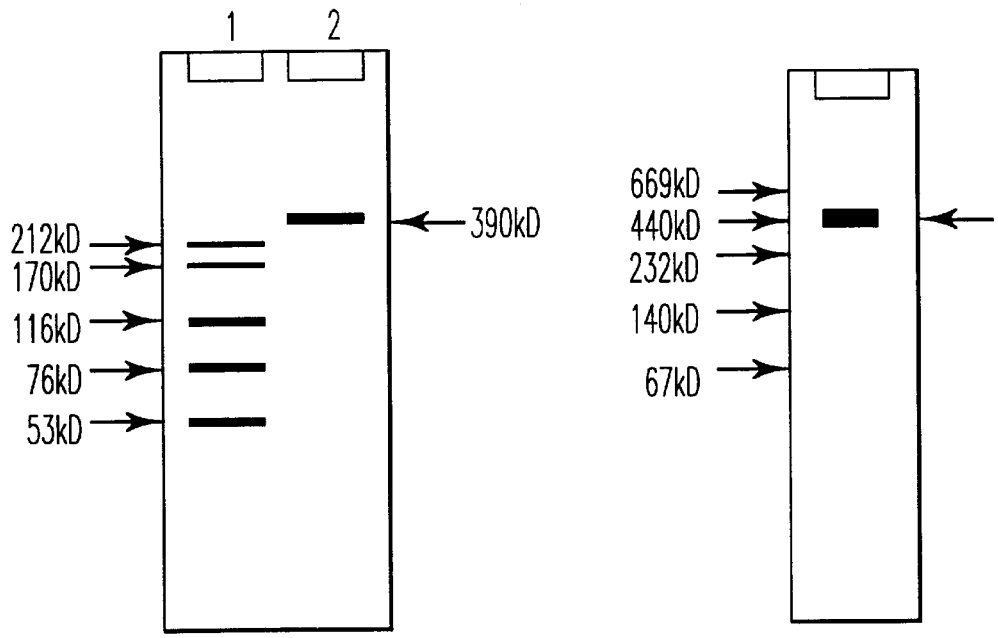
LANE 1: MOLECULAR WEIGHT MARKER
LANE 2: 20 μg GX
FIG. 4
FIG. 7
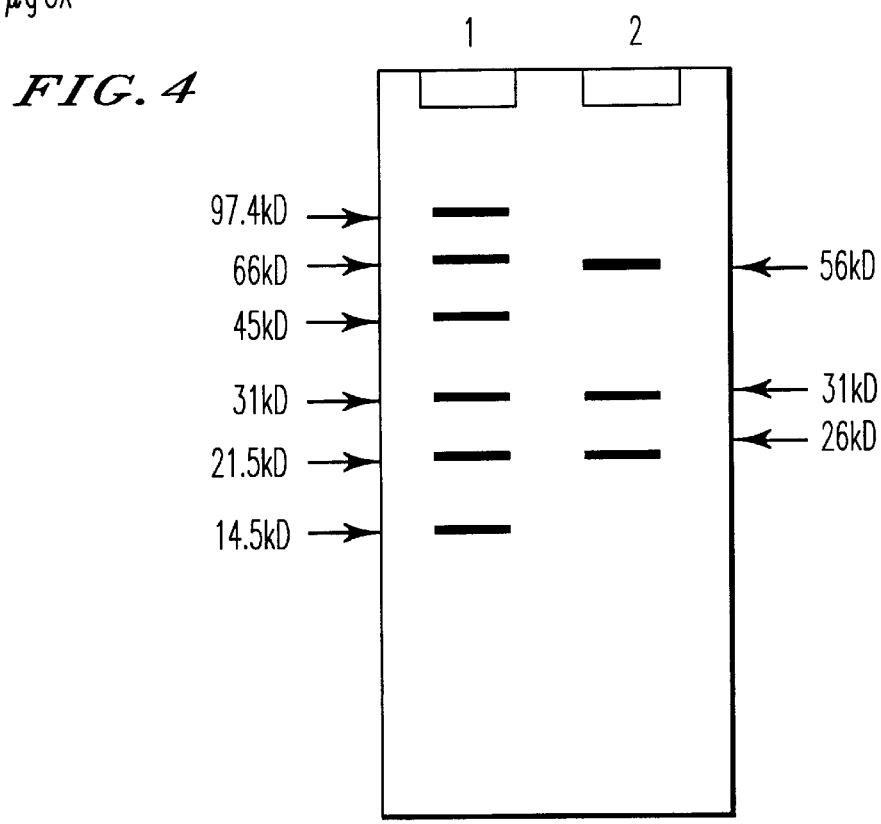
FIG. 5
LANE 1: MOLECULAR WEIGHT MARKER
LANE 2: 20 μg GX

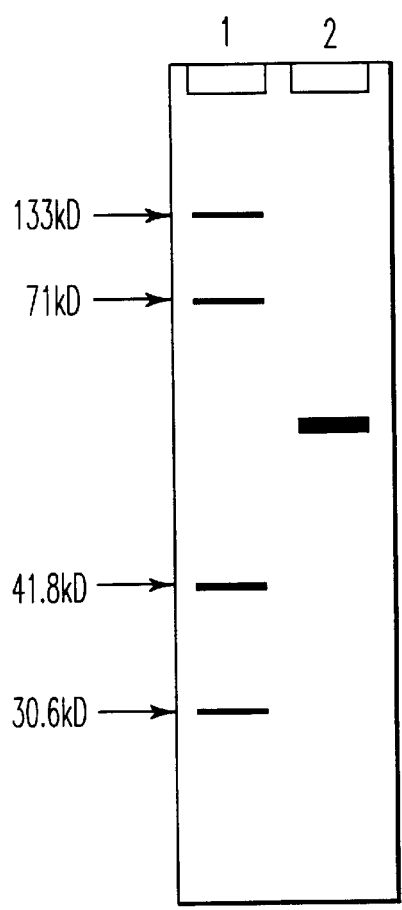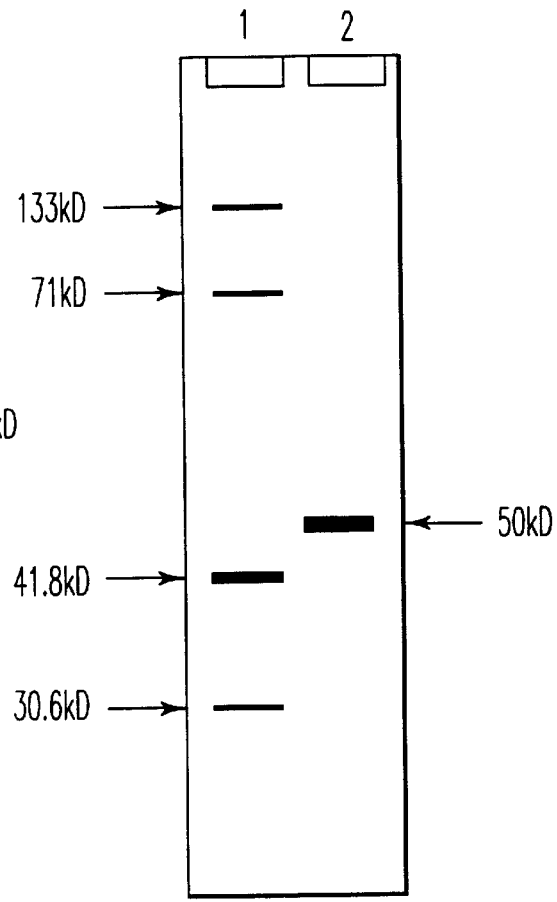
FIG. 12
FIG. 13

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1056 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Glycine max ( i x ) FEATURE:
        ( A ) NAME/KEY: CDS
        ( B ) LOCATION: 1..1056
        ( D ) OTHER INFORMATION: /note= "METHOD OF DETERMINING THE
            CHARACTERISTICS: P"

( i x ) FEATURE:
        ( A ) NAME/KEY: misc_feature
        ( B ) LOCATION: 1..9
        ( D ) OTHER INFORMATION: /note= "INSERTION SEQUENCE, METHOD
            OF DETERMINING THE CHARACTERISTICS: E"

( x i ) SEQUENCE DESCRIPTION: SEQ ID NO:1:

| ATG | GCT | AGG | TAC | GAC | AGC | GCC | CAC | GCG | GAC | AAG | GCC | GCC | ACG | TTG | CGC | 4 8 |

```
         Met Ala Arg Tyr Asp Ser Ala His Ala Asp Lys Ala Ala Thr Leu Arg
         1               5                   10                  15

ACC GAG GAG GAG CTG ATG TCC ATG TAC GAG CAG TGG CTC GTG AAG CAC              96
Thr Glu Glu Glu Leu Met Ser Met Tyr Glu Gln Trp Leu Val Lys His
                20              25                      30

GGG AAG GTG TAC AAC GCG CTC GGC GAG AAG GAG AAG CGC TTC CAG ATC             144
Gly Lys Val Tyr Asn Ala Leu Gly Glu Lys Glu Lys Arg Phe Gln Ile
            35              40              45

TTC AAG GAC AAC CTG CGA TTC ATC GAC GAC CAC AAC TCC GCG GAG GAC             192
Phe Lys Asp Asn Leu Arg Phe Ile Asp Asp His Asn Ser Ala Glu Asp
        50              55              60

CGA ACC TAC AAG CTC GGA CTG AAC CGG TTC GCT GAT CTC ACC AAC GAG             240
Arg Thr Tyr Lys Leu Gly Leu Asn Arg Phe Ala Asp Leu Thr Asn Glu
65              70              75                      80

GAA TAC AGG GCC AAG TAC TTG GGA ACC AAG ATC GAT CCC AAC CGG AGG             288
Glu Tyr Arg Ala Lys Tyr Leu Gly Thr Lys Ile Asp Pro Asn Arg Arg
                85              90                  95

CTC GGA AAG ACC CCG AGC AAC CGC TAC GCG CCA CGT GTC GGC GAC AAA             336
Leu Gly Lys Thr Pro Ser Asn Arg Tyr Ala Pro Arg Val Gly Asp Lys
            100             105                 110

TTG CCT GAT TCC GTT GAT TGG AGG AAG GAA GGT GCT GTT CCT CCT GTC             384
Leu Pro Asp Ser Val Asp Trp Arg Lys Glu Gly Ala Val Pro Pro Val
        115             120                 125

AAA GAC CAA GGA GGC TGT GGG AGC TGT TGG GCA TTC TCA GCA ATC GGT             432
Lys Asp Gln Gly Gly Cys Gly Ser Cys Trp Ala Phe Ser Ala Ile Gly
    130             135                 140

GCA GTA GAA GGA ATA AAT AAG ATA GTA ACA GGC GAA CTG ATT TCG TTA             480
Ala Val Glu Gly Ile Asn Lys Ile Val Thr Gly Glu Leu Ile Ser Leu
145             150                 155                 160

TCA GAA CAA GAA TTG GTG GAT TGT GAT ACT GGA TAT AAC CAA GGA TGC             528
Ser Glu Gln Glu Leu Val Asp Cys Asp Thr Gly Tyr Asn Gln Gly Cys
                165                 170                 175

AAT GGA GGA CTT ATG GAC TAT GCA TTT GAG TTC ATA ATC AAC AAT GGC             576
Asn Gly Gly Leu Met Asp Tyr Ala Phe Glu Phe Ile Ile Asn Asn Gly
            180                 185                 190

GGC ATT GAT TCT GAT GAG GAT TAC CCA TAC CGT GGT GTT GAT GGT AGA             624
Gly Ile Asp Ser Asp Glu Asp Tyr Pro Tyr Arg Gly Val Asp Gly Arg
        195                 200                 205

TGC GAC ACA TAT AGG AAA AAT GCT AAA GTC GTT TCT ATT GAT GAC TAC             672
Cys Asp Thr Tyr Arg Lys Asn Ala Lys Val Val Ser Ile Asp Asp Tyr
    210                 215                 220

GAA GAT GTT CCT GCC TAT GAT GAG TTA GCC TTG AAA AAG GCC GTT GCA             720
Glu Asp Val Pro Ala Tyr Asp Glu Leu Ala Leu Lys Lys Ala Val Ala
225                 230                 235                 240

AAT CAG CCC GTG AGC GTT GCT ATT GAA GGA GGG GGC AGG GAA TTT CAA             768
Asn Gln Pro Val Ser Val Ala Ile Glu Gly Gly Gly Arg Glu Phe Gln
                245                 250                 255

TTA TAT GTA TCT GGT GTA TTC ACG GGG AGA TGT GGC ACA GCA CTA GAT             816
Leu Tyr Val Ser Gly Val Phe Thr Gly Arg Cys Gly Thr Ala Leu Asp
            260                 265                 270

CAT GGT GTC GTG GCT GTT GGG TAT GGA ACA GCT AAA GGT CAT GAT TAT             864
His Gly Val Val Ala Val Gly Tyr Gly Thr Ala Lys Gly His Asp Tyr
        275                 280                 285

TGG ATC GTA AGG AAT TCA TGG GGT TCT AGC TGG GGA GAG GAT GGC TAC             912
Trp Ile Val Arg Asn Ser Trp Gly Ser Ser Trp Gly Glu Asp Gly Tyr
    290                 295                 300

ATC AGA TTA GAA AGA AAT CTT GCT AAC AGC AGA TCA GGC AAG TGT GGA             960
Ile Arg Leu Glu Arg Asn Leu Ala Asn Ser Arg Ser Gly Lys Cys Gly
305                 310                 315                 320

ATT GCA ATT GAG CCA TCT TAT CCC CTT AAG AAT GGT CCA AAT CCC CCT            1008
```

| | | | | | | | | | | | | | | | |
|---|---|---|---|---|---|---|---|---|---|---|---|---|---|---|---|
| Ile | Ala | Ile | Glu | Pro<br>325 | Ser | Tyr | Pro | Leu | Lys<br>330 | Asn | Gly | Pro | Asn | Pro<br>335 | Pro |

| | | | | | | | | | | | | | | | | |
|---|---|---|---|---|---|---|---|---|---|---|---|---|---|---|---|---|
| AAT | CCT | GGA | CCA | TCA | CCC | CCT | TCA | CCT | GTG | AAG | CCG | CCA | AAT | GTC | TGA | 1056 |
| Asn | Pro | Gly | Pro<br>340 | Ser | Pro | Pro | Ser<br>345 | Pro | Val | Lys | Pro | Pro | Asn<br>350 | Val | * | |

(2) INFORMATION FOR SEQ ID NO:2:

(i) SEQUENCE CHARACTERISTICS:
        (A) LENGTH: 351 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Met<br>1 | Ala | Arg | Tyr | Asp<br>5 | Ser | Ala | His | Ala | Asp<br>10 | Lys | Ala | Ala | Thr | Leu<br>15 | Arg |
| Thr | Glu | Glu | Glu<br>20 | Leu | Met | Ser | Met | Tyr<br>25 | Glu | Gln | Trp | Leu | Val<br>30 | Lys | His |
| Gly | Lys | Val<br>35 | Tyr | Asn | Ala | Leu | Gly<br>40 | Glu | Lys | Glu | Lys | Arg<br>45 | Phe | Gln | Ile |
| Phe | Lys<br>50 | Asp | Asn | Leu | Arg | Phe<br>55 | Ile | Asp | Asp | His | Asn<br>60 | Ser | Ala | Glu | Asp |
| Arg<br>65 | Thr | Tyr | Lys | Leu | Gly<br>70 | Leu | Asn | Arg | Phe | Ala<br>75 | Asp | Leu | Thr | Asn | Glu<br>80 |
| Glu | Tyr | Arg | Ala | Lys<br>85 | Tyr | Leu | Gly | Thr | Lys<br>90 | Ile | Asp | Pro | Asn | Arg<br>95 | Arg |
| Leu | Gly | Lys | Thr<br>100 | Pro | Ser | Asn | Arg | Tyr<br>105 | Ala | Pro | Arg | Val | Gly<br>110 | Asp | Lys |
| Leu | Pro | Asp<br>115 | Ser | Val | Asp | Trp | Arg<br>120 | Lys | Glu | Gly | Ala | Val<br>125 | Pro | Pro | Val |
| Lys | Asp<br>130 | Gln | Gly | Gly | Cys | Gly<br>135 | Ser | Cys | Trp | Ala | Phe<br>140 | Ser | Ala | Ile | Gly |
| Ala<br>145 | Val | Glu | Gly | Ile | Asn<br>150 | Lys | Ile | Val | Thr | Gly<br>155 | Glu | Leu | Ile | Ser | Leu<br>160 |
| Ser | Glu | Gln | Glu | Leu<br>165 | Val | Asp | Cys | Asp | Thr<br>170 | Gly | Tyr | Asn | Gln | Gly<br>175 | Cys |
| Asn | Gly | Gly | Leu<br>180 | Met | Asp | Tyr | Ala | Phe<br>185 | Glu | Phe | Ile | Ile | Asn<br>190 | Asn | Gly |
| Gly | Ile | Asp<br>195 | Ser | Asp | Glu | Asp | Tyr<br>200 | Pro | Tyr | Arg | Gly | Val<br>205 | Asp | Gly | Arg |
| Cys | Asp<br>210 | Thr | Tyr | Arg | Lys | Asn<br>215 | Ala | Lys | Val | Val | Ser<br>220 | Ile | Asp | Asp | Tyr |
| Glu<br>225 | Asp | Val | Pro | Ala | Tyr<br>230 | Asp | Glu | Leu | Ala | Leu<br>235 | Lys | Lys | Ala | Val | Ala<br>240 |
| Asn | Gln | Pro | Val | Ser<br>245 | Val | Ala | Ile | Glu | Gly<br>250 | Gly | Gly | Arg | Glu | Phe<br>255 | Gln |
| Leu | Tyr | Val | Ser | Gly<br>260 | Val | Phe | Thr | Gly<br>265 | Arg | Cys | Gly | Thr | Ala<br>270 | Leu | Asp |
| His | Gly | Val<br>275 | Val | Ala | Val | Gly<br>280 | Tyr | Gly | Thr | Ala | Lys<br>285 | Gly | His | Asp | Tyr |
| Trp | Ile<br>290 | Val | Arg | Asn | Ser | Trp<br>295 | Gly | Ser | Ser | Trp<br>300 | Gly | Glu | Asp | Gly | Tyr |
| Ile<br>305 | Arg | Leu | Glu | Arg | Asn<br>310 | Leu | Ala | Asn | Ser | Arg<br>315 | Ser | Gly | Lys | Cys | Gly<br>320 |
| Ile | Ala | Ile | Glu | Pro | Ser | Tyr | Pro | Leu | Lys | Asn | Gly | Pro | Asn | Pro | Pro |

|   |   |   | 325 |   |   |   |   |   | 330 |   |   |   |   |   | 335 |
|---|---|---|---|---|---|---|---|---|---|---|---|---|---|---|---|
| Asn | Pro | Gly | Pro | Ser | Pro | Pro | Ser | Pro | Val | Lys | Pro | Pro | Asn | Val |   |
|   |   |   | 340 |   |   |   |   |   | 345 |   |   |   |   |   | 350 |

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

| Glu | Glu | Glu | Glu | Glu |
|---|---|---|---|---|
| 1 |   |   |   | 5 |

(2) INFORMATION FOR SEQ ID NO:4:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

| Glu | Glu | Glu | Glu | Glu | Met | Ala | Val | Val | Pro | Gln | Gly | Leu | Phe | Arg | Gly |
|---|---|---|---|---|---|---|---|---|---|---|---|---|---|---|---|
| 1 |   |   |   | 5 |   |   |   |   | 10 |   |   |   |   | 15 |   |

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:5:

AAGGAGTATA ACATATGGCT AGC      23

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:6:

ATGCATAAGC TT      12

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:7:

-continued

AAGGAGTATA ACATATGGCT AGGTAC 26

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic Primer"

( x i ) SEQUENCE DESCRIPTION: SEQ ID NO:8:

CAAATGTCTG AGACAACTAC T 21

AMINOPEPTIDASE GX, AND A METHOD OF HYDROLYZING A PROTEIN WITH THE SAME

BACKGROUND OF THE INVENTION

1. Field of the Invention

The present invention relates to a novel aminopeptidase and a method of hydrolyzing a peptide or protein by use of the aminopeptidase or a cell extract containing the aminopeptidase.

2. Discussion of the Background

An aminopeptidase is an enzyme which releases an N-terminal amino acid sequentially from a peptide or protein.

The decomposition of proteins such as soybean protein, wheat gluten, casein etc., particularly the decomposition of soybean protein into amino acids has been carried out conventionally using acid hydrolysis with hydrochloric acid or sulfuric acid or the conventional proteases derived from microorganisms, e.g. aspergillus (Japanese Patent laid-open Publication No. 70,852/1976, Japanese Patent Publication No. 32,344/1980, Japanese Patent laid-open Publication No. 239,966/1991, Japanese Patent laid-open Publication No. 239,966/1987, Japanese Patent laid-open Publication No. 2392/1990 and Japanese Patent laid-open Publication No. 112,461/1991).

The preparation of a soybean protein hydrolysate as a candidate for a natural seasoning by hydrolyzing soybean protein with an acid requires a reaction at 100° C. for 1 to 2 days, and at such a high-temperature and long reaction time requires high energy consumption. On the other hand, the acid hydrolysis of a protein is easy, but there are problems in that the resulting amino acids are also decomposed (destroyed) and a high salt content results from neutralization.

An approach to these problems was to decompose a protein under mild conditions by the use of a conventional protease. However, the conventional proteases, typically papain, subtilisin etc. are endopeptidases, and thus they decompose a protein into peptides, but only slightly decompose the peptides further into amino acids. Therefore, aspartic acid and glutamic acid participating strongly in taste were only slightly released, while bitter tastes were brought about, and the resulting hydrolysate cannot be used as a seasoning liquid.

To solve this problem, the combined use of exopeptidases, i.e. a group of enzymes decomposing a peptide into amino acids, such as aminopeptidase, carboxypeptidase etc., is considered effective. For example, the importance of leucine aminopeptidase and acid carboxypeptidase is mentioned to increase the content of free amino acids for decomposing soybean protein with aspergillus, typically for making soy sauce by fermentation (Tadanobu Nakadai, Shouken, Vol. 11, No. 2, (1985)).

In this literature, however it is also described that in soy sauce there still remain dipeptides and tripeptides containing acidic amino acids in their sequences and these peptides are only slightly decomposed with a peptidase derived from aspergillus. Further, these dipeptides and tripeptides also include a large number of peptides containing glutamic acid or aspartic acid at the N-terminal end.

The term "peptides only slightly decomposed" as used herein means that an enzyme serving as the catalyst for decomposition, that is, a peptidase, has low substrate specificity for them.

This poor ability to decompose dipeptides and tripeptides containing acidic amino acids in their sequences is not only a problem with the peptidase derived from aspergillus in making soy sauce by fermentation, but also a problem with commercial peptidase preparations, typically those derived from aspergillus.

In the soy sauce industry etc., therefore, there is a demand for the discovery of a peptidase which effectively decomposes low-molecular-weight peptides containing glutamic acid and aspartic acid in their sequences in order to raise the degree of released amino acids in a peptide or protein hydrolysate.

SUMMARY OF THE INVENTION

The present inventors searched soybean cotyledons for a clue to solving the above problem. The proteins stored in soybeans are decomposed completely into amino acids in a very short time as soybeans germinate. The present inventors expected the germinated soybeans to contain a certain peptidase which can easily decompose even difficult to decompose peptides derived from the storage proteins.

In particular, the inventors thought that there might be a peptidase with substrate specificity and properties by which glycinin and β-conglisinin, which are present as major storage proteins containing acidic amino acid-enriched motifs with, e.g. successive acidic amino acids such as -Glu-Glu-Glu-Glu-Glu-(SEQ ID NO:3), could be decomposed completely into amino acids.

As proteolytic enzymes found in germinated soybeans, the followings have already been reported: 7S globulin protease (K. A. Wilson et al., Plant Physiol. 82, 71 (1986), X. Qi et al., Plant Physiol. 99, 725 (1992)), 11S globulin protease (K. A. Wilson et al., Plant Physiol. 82, 71 (1986), K. A. Wilson et al., Plant Physiol. 88, 355 (1988)), Bowman-Birk type trypsin inhibitor protease (M. A. Madden et al., Phytochemistry 24, 2811 (1985)), Qunitz type trypsin inhibitor protease (P. M. Hartl et al., Phytochemistry 25, 23 (1986), K. A. Wilson et al., Plant Physiol. 88, 355 (1988)), serine protease (M. Akhtaruzzaman et al., Biosci. Biotech. Biochem. 56(6), 878 (1992), novel thiol protease D3 (Japanese Patent laid-open Publication No. 264/1996 published on Jan. 8, 1996, and Japanese Patent Application No. 353,931/1995)).

However, these enzymes are endopeptidases and are thus not suitable for decomposing an acidic amino acid-containing peptide into amino acids.

Further, carboxypeptidase (Sachiho Kubota, Yakugaku Zasshi 96(5), 639 (1976)) and aminopeptidase (Shinji Watanabe et al., Nippon Nogei Kagakkaishi 63(3), 617 (1989)) have been reported as exopeptidases, but these are not suitable for decomposing an acidic amino acid-containing peptide into amino acids.

Therefore, the object of the present invention is to provide an aminopeptidase which effectively decomposes a low-molecular-weight peptide whose sequence contains glutamic acid and aspartic acid present in a soybean hydrolysate etc. as well as a method of hydrolyzing a peptide or protein by use of the aminopeptidase.

It has now been found that an enzyme which can be used for decomposing a peptide containing acidic amino acids is present in an extract from germinated soybean cotyledons.

BRIEF DESCRIPTION OF THE DRAWINGS

FIG. 4 shows a profile in SDS-PAGE of the purified aminopeptidase GX stained with Coomassie, where the sample was not heated nor reduced, FIG. 5 shows a profile in SDS-PAGE of the purified aminopeptidase GX stained with Coomassie, where the sample was heated and reduced.

FIG. 7 shows a profile in SDS-PAGE of the purified aminopeptidase GX subjected to activity staining, where the sample was not heated nor reduced.

FIG. 12 shows a profile in SDS-PAGE of the purified aminopeptidase DLAP 1 subjected to activity staining, where the sample was not heated nor reduced.

FIG. 13 shows a profile in SDS-PAGE of the purified aminopeptidase DLAP2 subjected to activity staining, where the sample was not heated nor reduced.

DETAILED DESCRIPTION OF THE PREFERRED EMBODIMENTS

Figure 1:
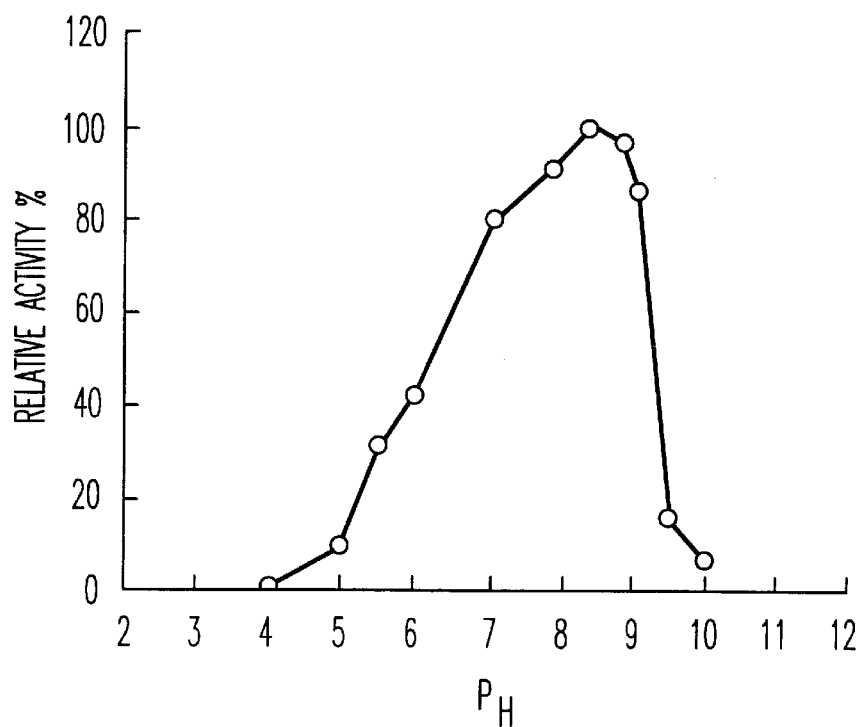
FIG. 1 shows a pH profile of aminopeptidase GX activity at different pH values.

The present invention provides aminopeptidase GX having an activity of decomposing a peptide or protein having acidic amino acids such as L-α-glutamylglutamic acid (Glu-Glu) etc. at the N-terminal end thereof.

The aminopeptidase GX of the present invention possesses the following properties:

a) optimum pH: about 5.5 to about 9.5;

b) optimum temperature: about 25 to about 60° C.;

c) temperature stability: keeping about 80% or more activity after left at 50° C. for 80 minutes or about 40% or more activity after left at 60° C. for 40 minutes;

d) molecular weight: about 400 to 550 kD (gel filtration), about 380 to 460 kD (native PAGE), and about 53 to 60 kD, about 30 to 32 kD, and about 25 to 28 kD (SDS-PAGE after reduction and heating);

e) substrate specificity: decomposing a peptide or protein containing glutamic acid or aspartic acid at the N-terminal to release the glutamic acid or aspartic acid;

f) inhibitors: inhibited by leuhistin, actinonin, alphamenine A or 1,10-orthophenanthroline; and g) effect of metal ions: inhibited by magnesium or copper.

A typical example of the aminopeptidase GX of the present invention is that derived from germinated soybean cotyledons.

In addition, the present invention provides a method of hydrolyzing a peptide or protein by allowing aminopeptidase GX to contact and react with a peptide or protein, as well as a method of hydrolyzing a peptide or protein by allowing a cell extract obtained by disrupting germinated soybean cotyledons containing aminopeptidase GX to contact and react with a peptide or protein.

Further, the present invention provides a method of hydrolyzing a peptide or protein by allowing a combination of the aminopeptidase GX and protease D3 (Japanese Patent laid-open Publication No. 264/1996 and Japanese Patent Application No. 353,931/1995) to contact and react with a peptide or protein.

Furthermore, the present invention provides a method of hydrolyzing a peptide or protein by allowing a combination of aminopeptidase GX, protease D3 and leucine aminopeptidase to contact and react with a peptide or protein.

Protease D3 is an enzyme purified from an extract of germinated soybean cotyledons and its properties and purification method are described in detail in Japanese Patent laid-open Publication No. 264/1996. Recombinant protease D3 was also prepared in *E. coli* (Japanese Patent Application No. 353,931/1995), and its details will be described in Example 11.

The protease D3 used is preferably in the form of a high-purity preparation, but may be a crude enzyme prepared from germinated soybean cotyledons.

The leucine aminopeptidase used may be a commercially available enzyme (e.g. No. 1503 available from Sigma) but is preferably a group of crude daizdu (soybean) leucine aminopeptidases obtained from an extract of germinated soybeans. There are 2 kinds of aminopeptidases in an extract of germinated soybeans as the daizdu (soybean) leucine aminopeptidase (DLAP), that is DLAP1 and DLAP2. DLAP1 and DLAP2 are very similar in properties to those of soybean-derived aminopeptidase which has already been reported (Shinji Watanabe et al., Nippon Nogei Kagakkaishi 63(3), 617 (1989)), but there is no positive proof that they are the same. The preparation of DLAP1 and DLAP2 will be described in Example 14.

DLAP 1 is an aminopeptidase with the following properties:

a) optimum pH: about 5.5 to about 9.5;

b) optimum temperature: about 25° to about 60° C.;

c) temperature stability: keeping about 90% or more activity after left at 50° C. for 60 minutes, or keeping about 25% or more activity after left at 60° C. for 10 minutes;

d) molecular weight: about 60 to 70 kD (native PAGE, activity staining);

e) substrate specificity: decomposing a peptide or protein containing leucine, alanine, glycine, phenylalanine, lysin, arginine, methionine, etc. at the N-terminal to release the corresponding amino acid; and f) inhibitors: inhibited by amastatine or actinonin.

DLAP2 is an aminopeptidase with the following properties:

a) optimum pH: about 5.0 to about 9.0;

b) optimum temperature: about 30° to about 70° C.;

c) molecular weight: about 45 to 55 kD (native PAGE, activity staining);

d) substrate specificity: decomposing a peptide or protein containing phenylalanine etc. at the N-terminal to release the phenylalanine etc; and e) inhibitors: inhibited by actinonin or phenylmethane sulfonyl fluoride.

The type of germinated soybeans preferably used as a material for preparing the novel aminopeptidase of the present invention is not limited. That is, the cultivation area and variety of the soybeans are not limited; commercially available soybeans, or those used as raw materials to extract oil, are not limited. There is no limitation to their germination method and cultivation conditions, and they can be used regardless of the presence or absence of sprouts and the term after their germination, but germinated soybeans preferably used as raw materials are those grown for 7 days after are were allowed to absorb water.

To prepare the novel aminopeptidase GX of the present invention, soybeans, preferably those described above, are used as a source from which to extract the enzyme. Preferably, cotyledons are removed from the soybeans and used as a source of the enzyme. For industrial application of the novel aminopeptidase of the present invention, this extract from soybeans can be used as such, or its crude or purified preparation can also be used.

The purification of the novel aminopeptidase of the present invention will be described in detail in Example 3. The preparation of a cell extract obtained by disrupting germinated soybean cotyledons will also be described in detail in the Examples below.

The novel aminopeptidase GX of the present invention will act on an protein or oligopeptide having glutamic acid or aspartic acid at the N-terminal end, among usual proteins such as casein, bovine serum albumin, hemoglobin, soybean protein or peptides derived from the foregoing usual proteins, thus releasing glutamic acid or aspartic acid. Further, the novel aminopeptidase GX will act on peptides generally only slightly decomposed with exopeptidases (known aminopeptidase, carboxypeptidase), such as a dipeptides having an acidic amino acid at the N-terminal end, a biologically active peptide having an acidic amino acid at the N-terminal end, and α-polyglutamic acid, to release their N-terminal acidic amino acid (see Examples 7, 8, 9 and 10 below).

The optimum pH of the novel aminopeptidase GX of the present invention is in the range of about 5.5 to 9.5, preferably about pH 7 to about 9 (see FIG. 1). Therefore, the peptide or protein should be hydrolyzed in this pH range.

The optimum temperature of the novel aminopeptidase GX is in the range of about 25° to 60° C., preferably about 35° to 55° C. (see FIG. 2). Therefore, the peptide or protein should be hydrolyzed in this temperature range.

The novel aminopeptidase GX is temperature stabile and maintains about 80% or more of the original activity even after incubation at 50° C. for 80 minutes or about 40% or more of the original activity after incubation at 60° C. for 40 minutes. Therefore, the hydrolysis reaction of the peptide or protein is carried out preferably at 50° C. or less in order to prevent the inactivation of the enzyme for a long time (see FIG. 3).

The effect of inhibitors on the novel aminopeptidase of the present invention was examined. The results indicate that the enzyme was strongly inhibited by aminopeptidase inhibitors such as leuhistine, actinonin etc. and weakly inhibited by aiphamenine A, 1,10-orthophenanthroline (i.e. metal chelate compound), magnesium chloride, copper chloride etc. (see Table 1). As can be seen from this result, the novel aminopeptidase GX of the present invention is an aminopeptidase where a metal is involved in its activity expression.

The estimated molecular weight of the novel aminopeptidase of the present invention is about 390 to 400 kD as determined in SDS-PAGE when the sample was not reduced nor heated (see FIG. 4). On the other hand, when the sample was reduced and heated, the enzyme was separated on SDS-PAGE into subunits with molecular weights of about 53 to 60 kD, about 30 to 32 kD, and 25 to 28 kD respectively (see FIG. 5).

Figure 6:
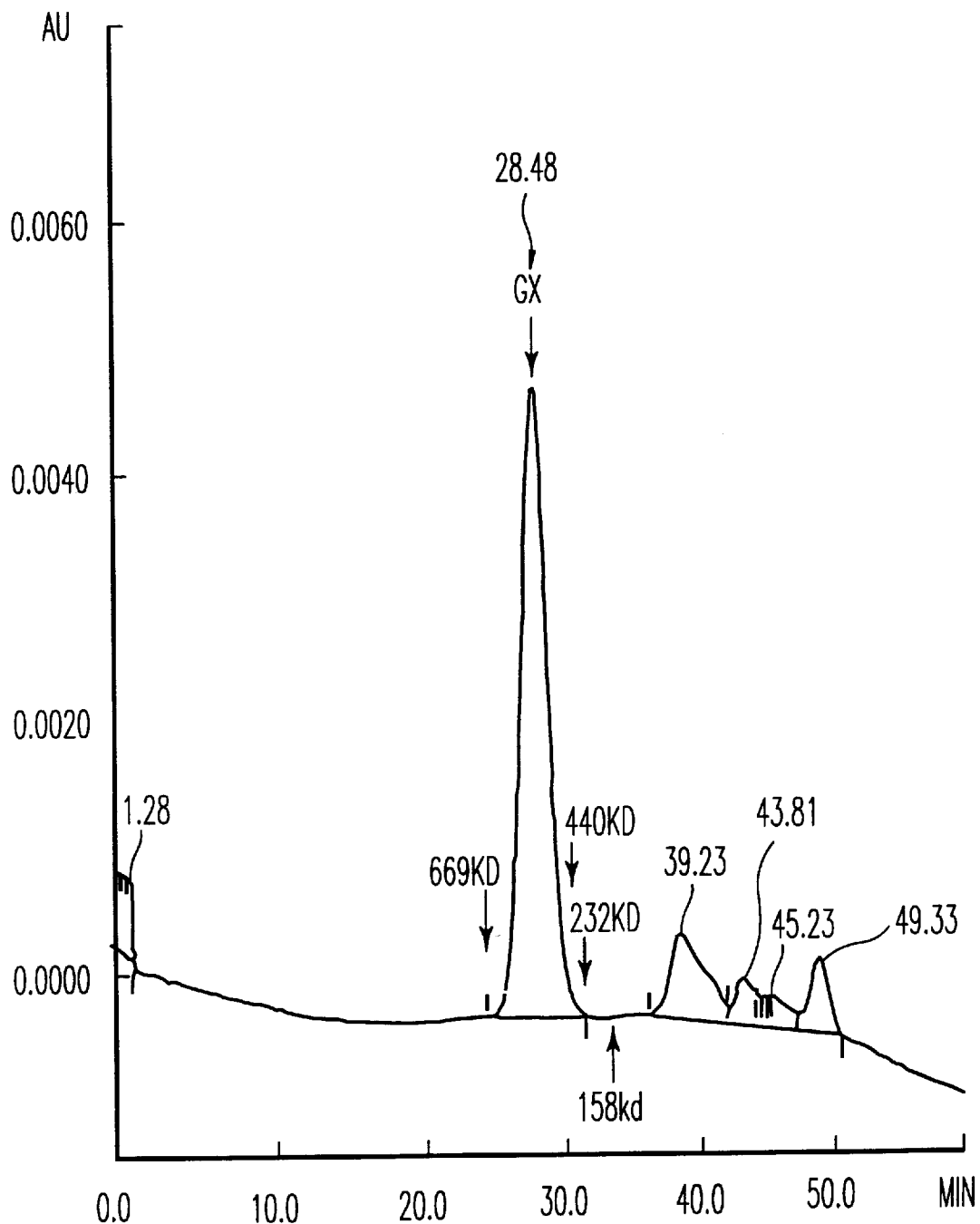
FIG. 6 shows the analysis of the molecular weight of the purified aminopeptidase GX by gel filtration through SUPEROSE 6.

The analysis of molecular weight of the purified enzyme by a gel filtration column indicated that the activity peak was present in a molecular weight of about 400 to 550 kD (see FIG. 6). Further, the molecular weight estimated by native PAGE was in the range of about 380 to 460 kD (see FIG. 7).

To obtain (a) an amino acid and peptide mixture or (b) protein hydrolysate with a high content of acidic amino acids, the novel aminopeptidase GX of the present invention as such, or a cell extract obtained by disrupting germinated soybean cotyledons, may be allowed to act on peptides or a protein hydrolysate after treatment with various proteases. For example, the decomposition of L-α-glutamylglutamic acid (Glu-Glu) with an extract of germinated soybeans in 50 mM sodium phosphate buffer (pH 8.0) in the presence of 2 mM sodium azide at 37° C. will result in significant release of glutamic acid from the substrate Glu-Glu. This decomposition also proceeds efficiently even in deionized water.

To obtain an amino acid mixture with a high content of acidic amino acids released from soybean protein, not only the novel aminopeptidase GX of the present invention as such, but a cell extract obtained by disrupting germinated soybean cotyledons may also be used to decompose a peptide mixture, that is, a protein hydrolysate treated with the enzyme cysteine protease D3 from germinated soybeans.

Alternatively, the peptide mixture treated with the enzyme cysteine protease D3 from germinated soybeans may be hydrolyzed with leucine aminopeptidase in combination with the aminopeptidase GX of the present invention, to give a hydrolysate with amino acids in high yield. For example, if the protein hydrolysate treated with cysteine protease D3 is subjected to hydrolysis at 42° C. with a combination of the novel aminopeptidase GX with DLAP 1 and DLAP2 (germinated soybean-derived leucine aminopeptidases) in amounts of 0.4 to 4 U GX, 10 to 130 U DLAP1 and 10 to 65 U DLAP2 per mg of the substrate in a solution adjusted to pH 8.0 with sodium hydroxide, the peptide will be decomposed to release various amino acids significantly (see the Examples below).

EXAMPLES

Hereinafter, the present invention is illustrated by reference to non-limiting Examples.

Example 1

Detection of Peptidase Activity

The substrate used was dipeptide Glu-Glu, i.e. consisting of glutamic acids, and the glutamic acid released by the action of the enzyme was determined. The glutamic acid was quantitatively determined using conventional amino acid analysis means with ninhydrin or YAMASA GLUTAMIC ACID ASSAY KIT commercially available. Unless otherwise specified, the following conditions and method were used.

0.05 ml enzyme solution, 0.02 ml of 50 mM L-α-glutamylglutamic acid, 0.02 ml of 100 mM N-2-hydroxyethylpiperazine-N'-2-ethanesulfonic acid (HEPES) buffer (pH 7.2), and 0.11 ml H$_2$O were mixed and reacted at 37° C. for 20 minutes. The reaction was stopped by adding 0.05 ml of 50% aqueous acetic acid, and the glutamic acid released in the reaction solution was quantitatively determined. The activity of the enzyme causing release of 2 $\mu$M glutamic acid from L-α-glutamylglutamic acid per minute was assumed to be 1 Unit.

Example 2
Search for L-α-Glutamylglutamic Acid (Glu-Glu) Decomposing Peptidase

The above detection method was used to search for decomposition activity in an extract of germinated soybean cotyledons. First, the extract of cotyledons 7 days after germination was examined for Glu-Glu decomposition activity.

To cotyledons 7 days after germination, 4 g (8 cotyledons), was added a 5-fold excess volume (20 ml) of an ice-cold buffer (20 mM potassium phosphate buffer pH 7.0, 200 mM NaCl, 10 mM 2-mercaptoethanol, 2 mM $NaN_3$), and the cotyledons were disrupted with a homogenizer, extracted, filtered through a gauze. The filtrate was centrifuged at 32,000 g for 30 minutes at 4° C. The supernatant was filtered through a filter paper to give a crude extract. In this crude extract, the enzyme activity was present.

Example 3
Purification of L-α-glutamylglutamic Acid (Glu-Glu) Decomposing Peptidase Because the L-α-glutamylglutamic acid (Glu-Glu) decomposition activity was present in the extract from cotyledons 7 days after germination, the enzyme with this activity was designated GX, and the purification of GX was carried out in the following manner.

1. Extraction

To 600 g cotyledons 7 days after seeding was added a 5-fold excess volume (3000 ml) of an ice-cold buffer (20 mM potassium phosphate buffer pH 7.0, 200 mM NaCl, 0.1 mM PEFABLOC SC (4-(2-aminoethyl)-benzenesulfonyl fluoride HCl), 10 $\mu$M E-64, 10 mM 2-mercaptoethanol, 2 mM $NaN_3$), and the cotyledons were disrupted with a homogenizer, extracted, and filtered through a gauze. The filtrate was centrifuged at 32,000 g for 30 minutes at 4° C. The supernatant was filtered through a filter paper (No. 514 A, available from Advantech Toyo K.K.). The crude extract obtained as the filtrate was concentrated in a membrane concentration unit (MINITAN, available from Millipore).

2. Ammonium Sulfate Fractionation

The pH of the crude extract thus prepared was confirmed (adjusted to pH 7.0 with NaOH), and this solution was made 40% saturation with ammonium sulfate by adding ammonium sulfate (763 g/3150 ml). The solution was stirred at 4° C. for 6 hours and centrifuged at 32,000 g for 30 minutes at 4° C. to give a supernatant. The supernatant was made 65% saturation with ammonium sulfate by further adding ammonium sulfate (564 g/3,400 ml). It was stirred at 4° C. overnight (15 hours) and then centrifuged at 32,000 g for 30 minutes at 4° C. to recover precipitates. The precipitates were dissolved in 120 ml buffer (50 mM potassium phosphate buffer pH 7.0, 100 mM NaCl, 2 mM $NaN_3$) and dialyzed repeatedly against a buffer (2L×5, 16 hours) at 7° C. After dialysis, the dialysate was centrifuged at 32,000 g for 20 minutes at 4° C. and then filtered thorough a 0.2 $\mu$m filter (NALGENE filterware) to be applied to anion exchange chromatography in the subsequent step.

3. Anion Exchange Chromatography

The sample obtained in 2 above was fractionated through HILOAD 26/10 Q SEPHAROSE HP in FPLC system (Pharmacia) as follows. About 190 ml sample was divided due to a large volume into 8 aliquots and each aliquot was subjected to this ion-exchange chromatography. The column was previously equilibrated with the same buffer as used in the previous dialysis, and after application of the sample, the column was washed with a 5-fold column volume of the buffer. After washing, the adsorbed active fraction was eluted with an increasing linear gradient of from 100 mM to 250 mM NaCl in an 8-fold column volume of the buffer. The active fraction was collected (2000 ml) and concentrated to 90 ml in an ultrafiltration unit (MINITAN, manufactured by Millipore). The sample was adjusted to 1M ammonium sulfate by adding 11.88 g ammonium sulfate. The solution was centrifuged at 32,000 g for 10 minutes at 4° C. to give a supernatant to be applied to hydrophobic chromatography in the subsequent step.

4. Hydrophobic Chromatography

The sample obtained in 3 above was fractionated thorough HILOAD 26/10 PHENYL SEPHAROSE HP in the FPLC system as follows. The sample was divided into 2 aliquots and each aliquot was applied to the column. The column was previously equilibrated with a buffer (50 mM potassium phosphate buffer pH 7.0, 1M $(NH_4)_2SO_4$, 2 mM $NaN_3$), and after addition of the sample, the column was washed with a 5-fold column volume of the buffer. The adsorbed active component was then fractionated in a decreasing linear gradient of from 1M to 0M ammonium sulfate in the buffer. The active fraction, 180 ml, was concentrated to 9.8 ml by an ultracentrifugation unit (MINITAN (Millipore) and CENTRIPREP 10 (Amicon)). The condensate was centrifuged at 32,000 g for 10 minutes at 4° C. to give a supernatant to be applied to gel filtration in the subsequent step.

5. Gel Filtration Chromatography

The sample obtained in 4 above was fractionated by gel filtration through HILOAD 26/60 SUPERDEX 200pg in the FPLC system as follows. The sample was divided into 2 aliquots and each aliquot was subjected to chromatography. The column was previously equilibrated with a buffer (50 mM potassium phosphate buffer pH 7.0, 100 mM NaCl, 2 mM $NaN_3$) and the sample was fractionated through it. The active fraction was concentrated to give a purified enzyme. The molecular weight of the purified enzyme was estimated to be 390 to 400 kD in SDS-PAGE when not subjected to reduction nor thermal treatment (see FIG. 4). When subjected to reduction and thermal treatment, the enzyme was separated into subunits having molecular weights of about 53 to 60 kD, about 30 to 32 kD and about 25 to 28 kD in SDS-PAGE respectively (see FIG. 5). When the purified enzyme was analyzed for molecular weight further by gel filtration on a gel filtration column SUPEROSE 6 (Pharmacia), an active peak appeared in a molecular weight of about 400 to 550 kD (see FIG. 6).

An increase in specific activity by a series of the purification steps was determined. The specific activity of the above crude GX enzyme solution for decomposition of Glu-Glu was about 7.6 mU/mg, while the specific activity of the purified enzyme GX was about 66 U/mg. This result indicated that in a series of the purification steps, the aminopeptidase GX was purified as highly by about 8700-fold in terms of specific activity.

Activity staining of the enzyme in native PAGE indicated that the molecular weight of the active enzyme was about 380–460 kD. Hereinafter, the active staining method is described.

Example 4
Peptidase Activity Staining in Native PAGE 20, 60, 120 mU enzyme was prepared in a Davis' sample preparation buffer (0.0625M Tris-HCl buffer pH 6.8, 15% glycerol, 0.001% bromophenol blue) and electrophoresed in a commercial gel (MULTIGEL 2/15, Dai-Ichi Kagaku Yakuhin K.K.) by using an electrophoresis buffer (3 g TRIS, 14.4 g/l glycine) at 5° C. The gel after electrophoresis was mixed with solution A (800 μl of 1M HEPES, pH 7.0, 300 μl of L-amino acid oxidase (1 mg/ml), 12.5 U peroxidase, 4 μl of 3-amino-4-ethylcarbazole (20 mM), 530 μl of 4-aminoantipyrine, 5840 μl of Glu-Phe (20 mM)) and solution B (8 ml of 2% aqueous agarose solution (55° C.)) and incubated in an incubator at 37° C. for 2 hours. The L-amino acid oxidase and peroxidase were purchased from Boehringer Mannheim, the 3-amino-4-ethylcarbazole were purchased from Dojin Kagaku K.K. and all the other reagents were purchased from Nakarai Tesque K.K. The results indicated that the active enzyme was found at a molecular weight of about 380 to 460 kD (see FIG. 7).

The enzymatic properties of the purified GX thus obtained are described below.

Example 5
Determination of Optimum pH and Optimum Temperature of Aminopeptidase GX A change in enzyme activity (optimum pH) due to reaction pH was determined in the following manner.

The enzyme reaction buffers used were sodium acetate buffer (pH 4.0, 4.5, 5.0, 5.5, 6.0), potassium phosphate buffer (pH 6.0, 7.0), Tris-HCl buffer (pH 7.0, 7.8, 8.3, 8.8), and sodium carbonate buffer (pH 9.0, 9.5, 10.0). 180 μl of 3.5 mU GX was prepared in 50 mM buffer at each pH and pre-incubated for 5 minutes at 30° C. 20 μl of the substrate Glu-Glu (5 mM for reaction) was added to each sample. It was stirred and incubated for 20 minutes. 20 μl of 1M sodium acetate buffer (pH 4.0) was added to stop the reaction.

The measurement results are shown in FIG. 1. As can be seen from FIG. 1, the optimum pH of the aminopeptidase GX of the present invention is in the range of about 5.5 to 9.5, preferably about 7 to about 9 (see FIG. 1).

The measurement of a change in enzyme activity due to reaction temperature (optimum temperature) was carried out as follows:

20 μl of the substrate Glu-Glu (5 mM for reaction) was added to 50 mM sodium acetate buffer (pH 6.0) and 180 μl of thus obtained reaction solution was pre-incubated for 5 minutes at each temperature (25°, 30°, 37°, 42°, 50°, 60°, 70° C.). 7 mU aminopeptidase GX was further added. This sample was stirred and incubated for 20 minutes. 20 μl of 1M sodium acetate buffer (pH 4.0) was added to stop the reaction.

Figure 2:
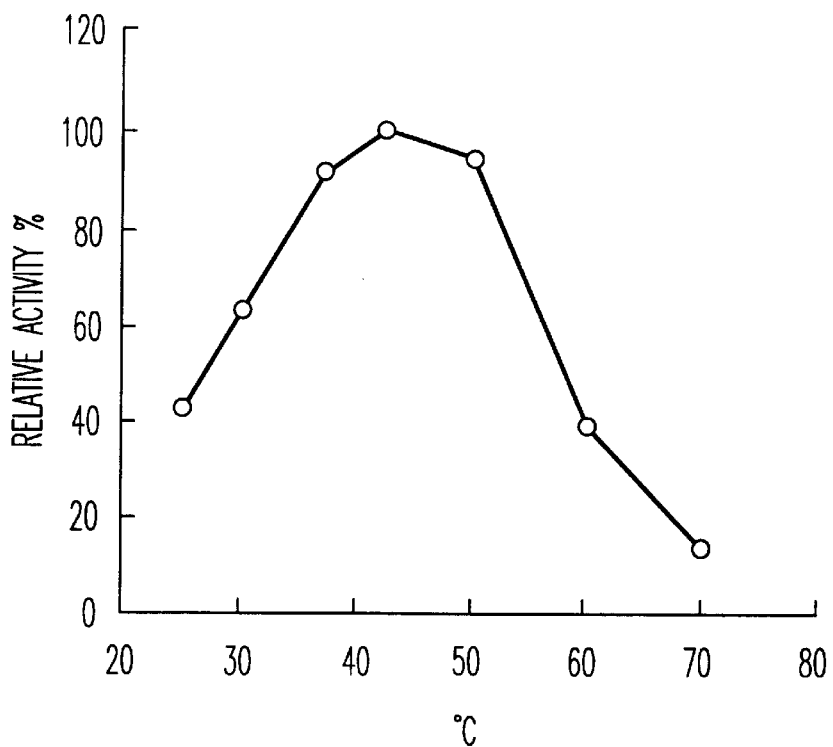
FIG. 2 shows a profile of aminopeptidase GX activity at different temperatures.

The measurement results are shown in FIG. 2. As can be seen from FIG. 2, the optimum temperature of the aminopeptidase GX of the present invention is in the range of about 25° to 60° C., preferably about 35° to 55° C. (see FIG. 2).

The determination of temperature stability was carried out as follows:

3.5 U/ml enzyme was incubated in a buffer (pH 6.0) at predetermined temperatures (25°, 30°, 37°, 42°, 50°, 60°, 70° C.) for predetermined times (10, 20, 30, 40, 80 minutes) and then examined for its remaining activity at 30° C.

Figure 3:
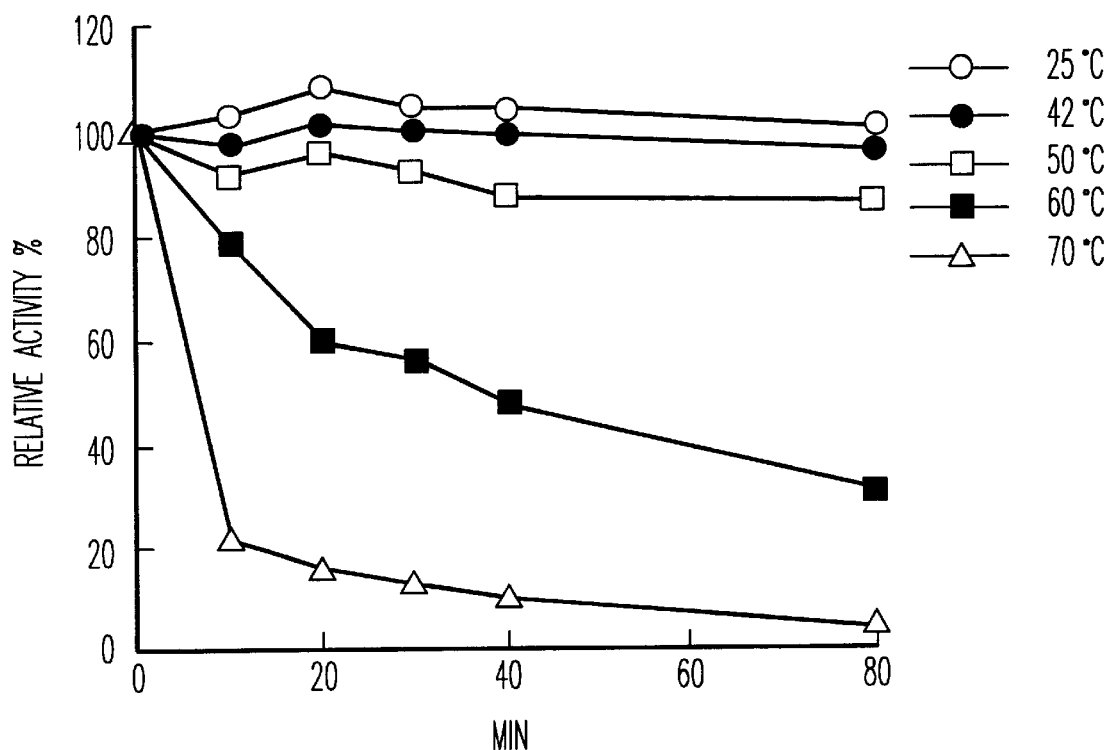
FIG. 3 shows a profile of the stability of aminopeptidase GX activity at different temperatures.

The measurement results are shown in FIG. 3. The enzyme of the present invention maintains about 80% or more activity even after 80-minute incubation at 50° C. or about 40% or more activity after 40-minute incubation at 60° C. Therefore, the reaction temperature for a long reaction is preferably 50° C. or less.

Example 6
Effect of Protease Inhibitors on GX

The effect of inhibitors and metals on the novel aminopeptidase GX of the present invention was examined. The inhibitors used were actinonin, amastatin, antipain, alphamenine A, diprotin A, leuhistin, phenylmethane sulfonyl fluoride (PMSF), trans-epoxysuccinyl-L-leucylamide (4-guanidino)-butane (E-64), iodoacetamide, and 1,10-orthophenanthroline, and the metals used were zinc chloride, manganese chloride, magnesium chloride and copper chloride. The 1,10-orthophenanthroline, zinc chloride, manganese chloride, magnesium chloride and copper chloride were purchased from Nakarai Tesque K.K. and all the other inhibitors were purchased from Peptide Institute, Inc.

In the presence of each inhibitor, the enzyme was left at room temperature (25° C.) for 20 minutes, and the remaining activity of the enzyme was determined in the same manner as in Example 1.

The results of activity measurement in the presence of each inhibitor are shown in Table 1. The aminopeptidase GX of the present invention was strongly inhibited by aminopeptidase inhibitors such as leuhistin and actinonin, and weakly inhibited by alphamenine A, 1,10-orthophenanthroline (i.e. metal chelate compound), magnesium chloride and copper chloride.

As can be seen from the foregoing, the aminopeptidase GX of the present invention is an aminopeptidase where a metal is involved in its activity expression.

TABLE 1

Effect of Each Protease Inhibitor on GX

| Inhibitor | Concentration | Remaining Activity (Relative Value %) |
|---|---|---|
| — | — | 100 |
| actinonin | 100 μM | 12 |
| amastatin | 100 μM | 100 |
| antipain | 100 μM | 100 |
| alphamenine A | 100 μM | 63 |
| diprotin A | 100 μM | 100 |
| E-64 | 10 μM | 100 |
| leuhistin | 100 μM | 0 |
| PMSF | 10 μM | 100 |
| iodoacetamide | 50 mM | 100 |
| orthophenanthroline | 10 μM | 47 |
| zinc chloride | 2 mM | 76 |
| manganese chloride | 2 mM | 88 |
| magnesium chloride | 2 mM | 32 |
| copper chloride | 2 mM | 56 |

Example 7
Substrate Specificity of GX for Dipeptide

To examine the substrate specificity of GX, the decomposing activity on various peptides was compared with the decomposing activity of decomposing Glu-Glu. The dipeptides used were Glu-Asp, Glu-Ser, Glu-Thr, Glu-Phe, Glu-Ala, Glu-Gly, Glu-Lys, γ-Glu-Glu, γ-Glu-Leu, Ser-Glu, Ala-Glu, Phe-Glu, Lys-Glu, Pro-Glu, Asp-Asp, Asp-Phe, Asp-Glu, Asp-Ala, Asp-Lys, Asp-ϵ-Lys, Gln-Gly and Gln-Gln, and the enzyme was allowed to act on each dipeptide in the same manner as in Example 1 using Glu-Glu as the substrate, then the amino acids in the reaction solution were quantified in amino acid analysis to compare the decomposition activity.

The results of the relative decomposition activity of GX for each dipeptide are shown in Table 2.

TABLE 2

Relative Decomposition Activity of GX for Each Dipeptide

| Dipeptide | Relative Decomposition Activity (%) |
|---|---|
| Glu-Glu | 100 |
| Glu-Lys | 175 |
| Glu-Gly | 80 |
| Glu-Ala | 108 |
| Glu-Phe | 32 |
| Glu-Thr | 102 |
| Glu-Ser | 128 |
| Glu-Asp | 63 |
| γ-Glu-Glu | 4 |
| Pro-Glu | 0 |
| Lys-Glu | 0 |
| Phe-Glu | 0 |
| Ala-Glu | 0 |
| Ser-Glu | 0 |
| Asp-ε-Lys | 11 |
| Asp-Lys | 172 |
| Asp-Ala | 110 |
| Asp-Glu | 30 |
| Asp-Phe | 79 |
| Asp-Asp | 14 |
| Gln-Gln | 0 |
| Gln-Gly | 0 |
| γ-Glu-Leu | 0 |

Example 8
Substrate Specificity of GX for Amino Acid Paranitroanilide Derivative, and Comparison with Aminopeptidase M To examine the substrate specificity of GX, the substrate specificity for each amino acid paranitroanilide derivative was compared with that for glutamic acid paranitroanilide (Glu-pNA). 0.05 ml enzyme solution, 0.02 ml of 2 mM each amino acid paranitroanilide, 0.02 ml of 100 mM HEPES buffer (pH 7.0), and 0.11 ml $H_2O$ were mixed and reacted at 37° C. for 20 minutes. The reaction was stopped by adding 0.05 ml of 50% aqueous acetic acid, and the amount of paranitroaniline released in the reaction solution was determined. For comparison, the enzyme activity causing release of 1 μmole paranitroaniline per minute from each amino acid paranitroanilide derivative was assumed to be 1 Unit. Its substrate activity was compared with that of aminopeptidase M (APASE M) which is an enzyme commercially available from Pierce company.

The results of the decomposition activity for amino acid paranitroanilide derivatives are shown in Table 3.

TABLE 3

| Synthetic Substrate | GX U/mg | APASE M (U/mg) |
|---|---|---|
| Glu-pNA | 65 | 2.8 |
| Leu-pNA | 0 | 1500 |
| Phe-pNA | 0 | 1100 |
| Gly-pNA | 0 | 100 |
| Ala-pNA | 0 | 2300 |
| Pro-pNA | 0 | 0.3 |

Example 9
Decomposition of Chromogranin A by GX

The decomposition of chromogranin A (Peptide Institute Inc.) i.e. an oligopeptide containing glutamic acid at the N-terminal by GX was examined.

0.02 ml buffer (500 mM ammonium carbonate), 0.05 ml of 5 mM chromogranin A, 0.08 ml $H_2O$, and 0.05 ml of 6 mU enzyme were reacted at 37° C. The reaction solution was sampled with time in an amount of 0.02 ml for each sampling. The reaction was stopped with 0.02 ml of 50% aqueous acetic acid. The reaction solution was analyzed for molecular weight by laser mass spectrum (KOMPAKT MALDI III, manufactured by Shimadzu Kratos).

Figure 8:
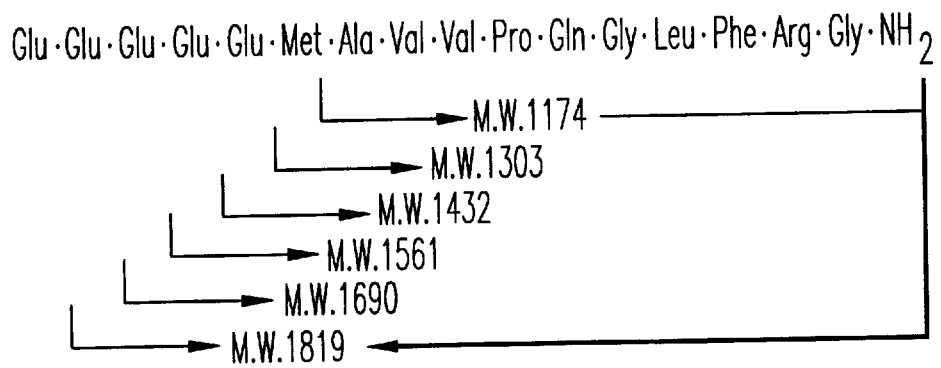
FIG. 8 shows a mass spectrum of a reaction solution in which chromogranin A was decomposed with aminopeptidase A, the structure of chromogranin A (SEQ ID NO:4), and masses of its respective fragments.
Figure 8:
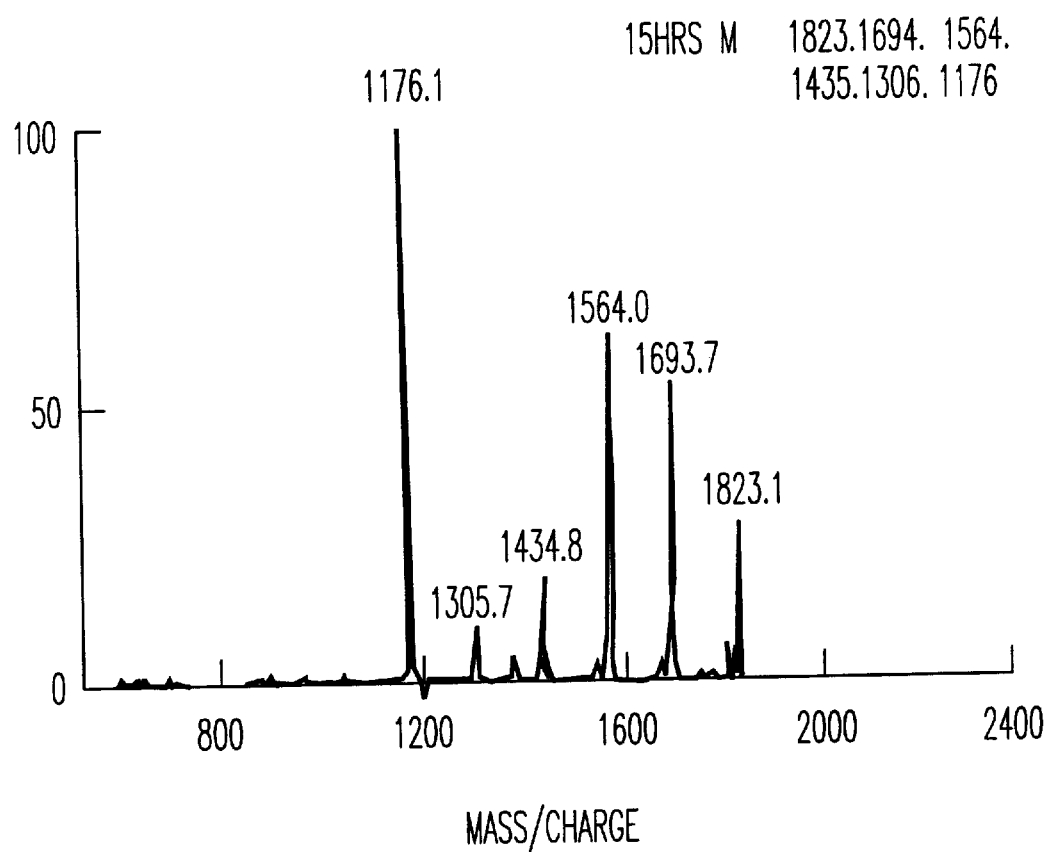

FIG. 8 shows a profile of the reaction solution after a 15-hour reaction. The molecular weights of 1823.1, 1693.7, 1564.0, 1434.8, 1305.7, and 1176.1 were observed and these results correspond to the molecular weights of chromogranin A and its fragments. GX had an aminopeptidase activity by which glutamic acid residues were released one by one from chromogranin A.

Example 10
Decomposition of α-polyglutamic Acid by GX

The decomposition of x-polyglutamic acid (molecular weight of 8000 or more) (Peptide Kenkyusho K.K.) by GX was examined.

Figure 9:
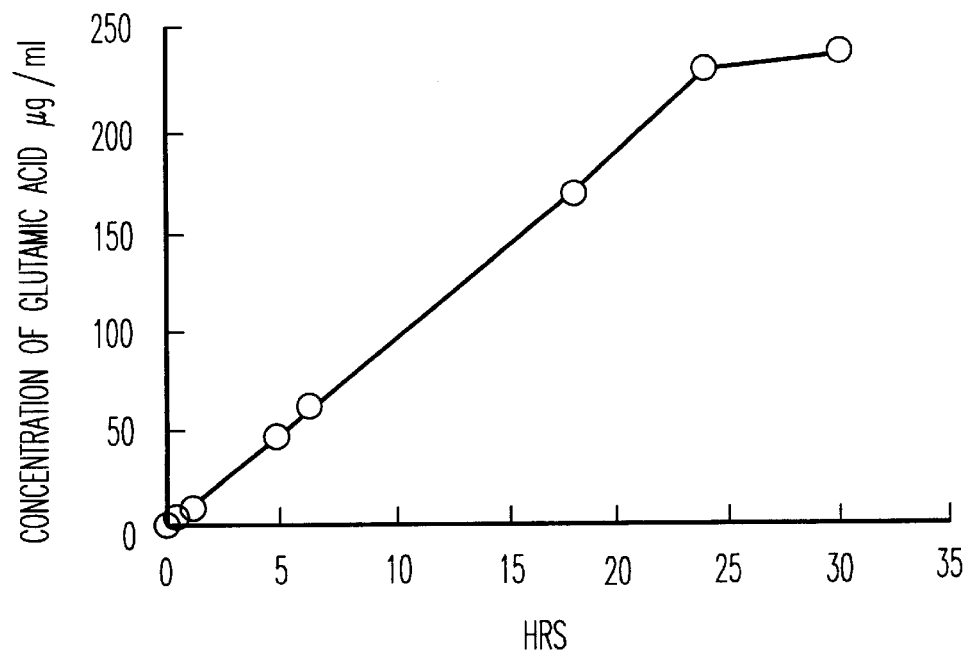
FIG. 9 shows an increase in glutamic acid when α-polyglutamic acid was decomposed with aminopeptidase GX.

0.05 ml of 100 mM HEPES buffer, 0.05 ml α-polyglutamic acid (50 mg/ml), 0.3 ml $H_2O$, and 0.1 ml of 100 mU enzyme were reacted at 37° C. The reaction solution was sampled with time in an amount of 0.02 ml for each sampling. The reaction was stopped with 0.02 ml of 50% aqueous acetic acid. The content of glutamic acid in the reaction solution was determined. The results are shown in FIG. 9.

Hereinafter, a preparation method for protease D3 derived from germinated soybean cotyledons, which was used in combination for decomposition of soybean protein, is described.

The method of detecting protease D3 derived from germinated soybean cotyledon, the definition of its activity unit, and the preparation method for this enzyme from an extract of germinated soybean cotyledons were described in detail in pending Japanese Patent laid-open Publication No. 264/1996 filed by the present inventors.

Protease D3 derived from germinated soybean cotyledons is a novel thiol protease which is enzyme 1 or 2 described in Japanese Patent Laid-Open Publication No. 264/1996 and either of the two can be used to decompose soybean protein.

In connection with protease D3, Japanese Patent Application No. 353,931/1995 filed on Dec. 28, 1995 by the present inventors, describes a process for producing recombinant protease D3 by use of CDNA and E.coli containing said cDNA Hereinafter, the recombinant protease D3 by use of E. coli is described.

As the recombinant protease D3 produced by E.coli, proteases D3-α and D3-β are described in Japanese Patent Application No. 353931/1995 and either of the two can be used to decompose soybean protein.

Example 11
Preparation of Recombinant Protease D3 by Use of E. coli

A cDNA library was prepared from mRNA derived from germinated soybean cotyledons, and a part of protease D3-β CDNA from this library was cloned in a usual manner and integrated into an expression vector capable of functioning in E. coli. E. coli transformed with this expression vector was cultured to yield a gene product as a protein inclusion body. This inclusion body was removed from the microorganism, then lyzed and unwound in vitro and allowed to contact a substrate with the pH shifted to the acid side. Hereinafter, this method is described in detail.

Figure 10:
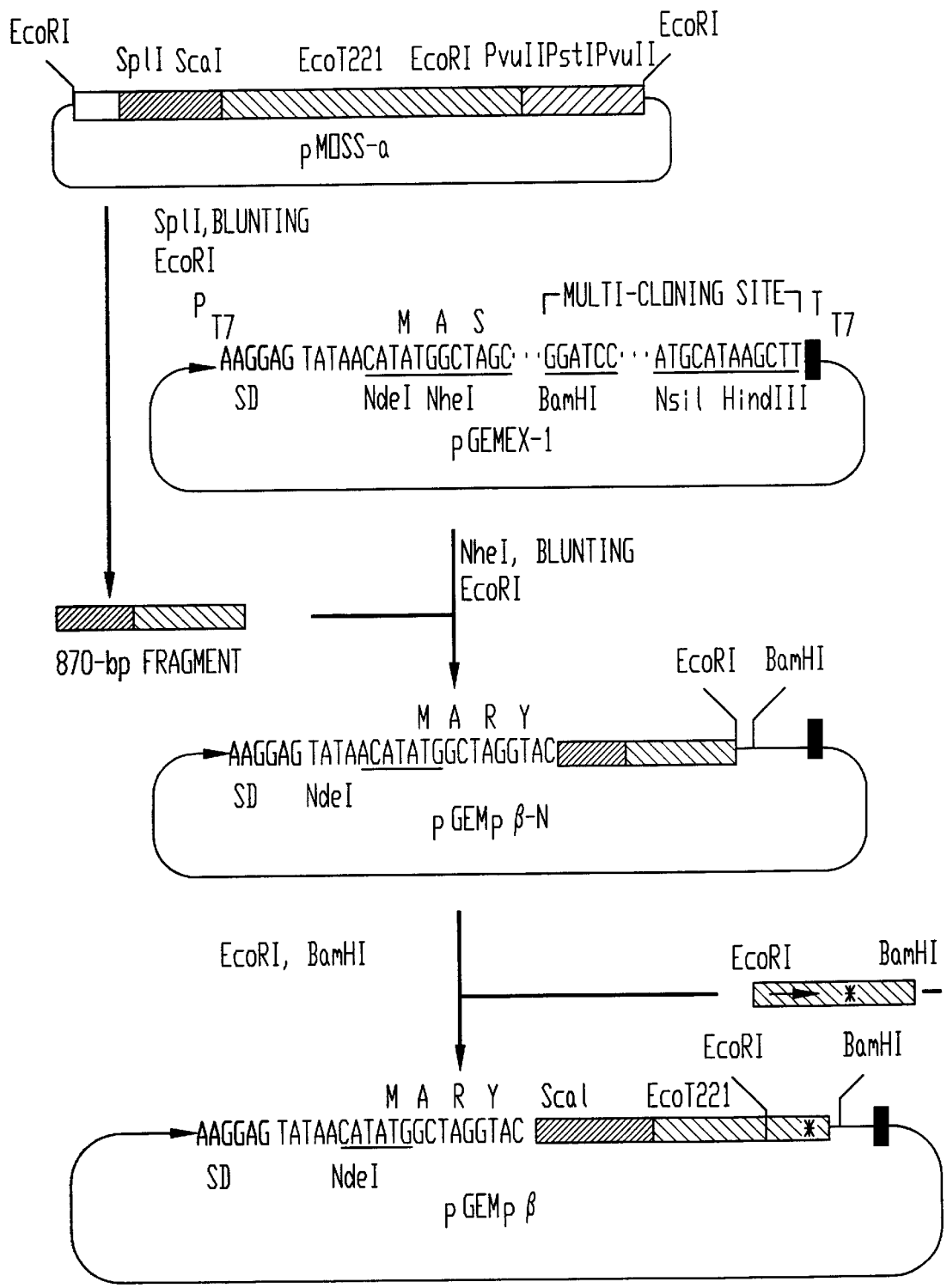
FIG. 10 shows the (partial) construction of expression plasmid pGEMpβ(SEQ ID NO:5,6,7).
Figure 11:
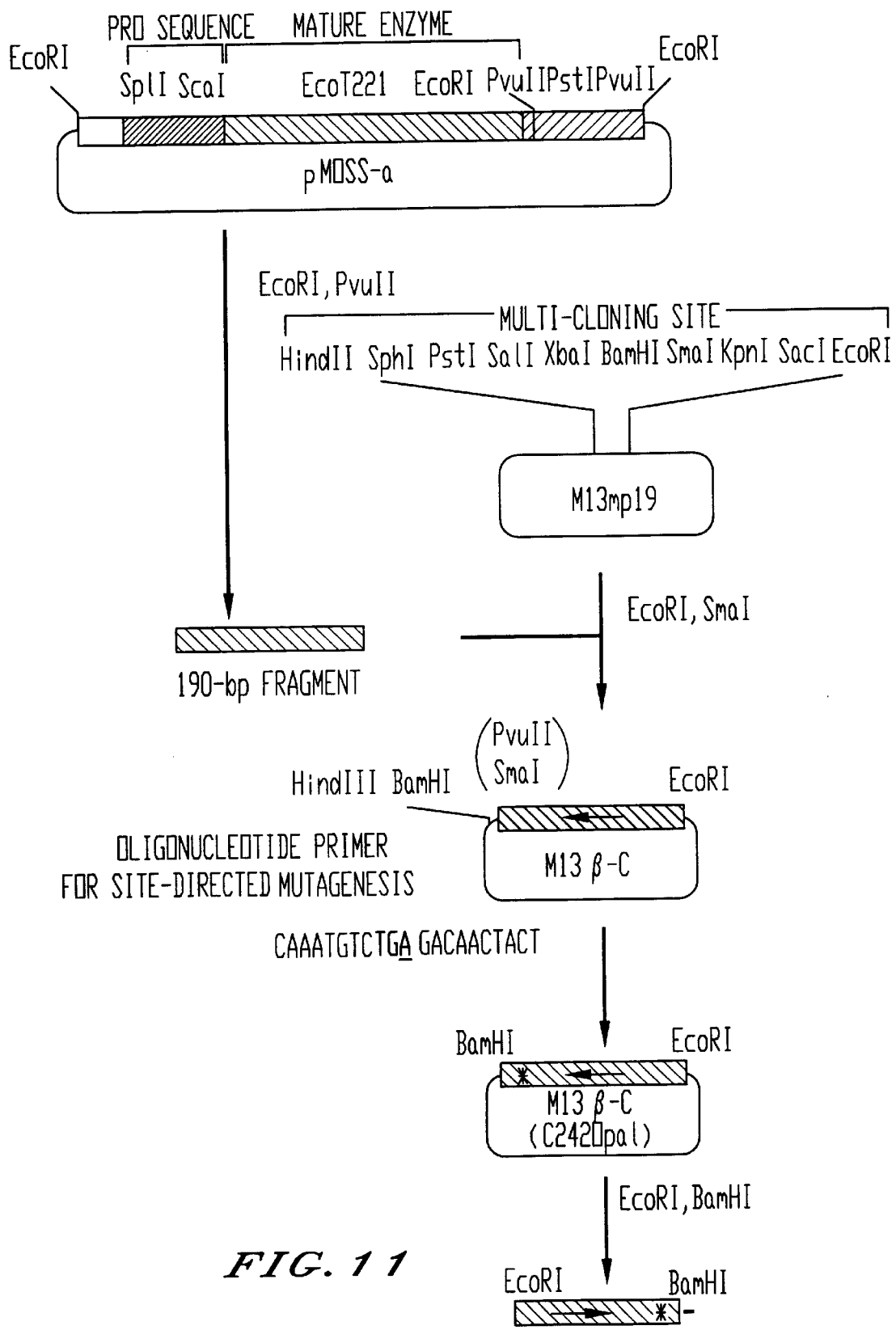
FIG. 11 shows the (partial) construction of expression plasmid pGEMpβ.

The construction of the expression plasmid is shown in FIGS. 10 and 11.

As shown in FIG. 10, clone pMOSS-a into which the whole-length D3-β CDNA had been integrated was cleaved with restriction enzyme SplI, then blunt-ended with Klenow enzyme, and next cleaved with EcoRI to give an about 870 bp fragment. A commercial expression vector pGEMEX-1 (Promega) was cleaved with NheI, then blunt-ended with Klenow enzyme, and cleaved with EcoRI to give a large fragment The above 870 kb fragment was ligated to this large fragment to give plasmid pGEMpβ-N.

Separately, as shown in FIG. 11, pMOSS-a was cleaved with EcoRI and PvuII to give a 190 bp fragment which was then inserted between EcoRI and SmaI sites on M13mp19 to construct M13β-C. Using a single-stranded DNA of M13β-C as a template and the oligonucleotide 5'-CAAATGTCTGAGACAACTACT-3' (SEQ ID NO: 8) as a mutagenesis primer, TGT (Cys codon at the 242-position in an open reading frame of D3-β CDNA) was mutated by site-directed mutagenesis into TGA (termination codon) in a sculptor in vitro mutagenesis system (Amersham company) to give M13β-C (C242Opal). It was then cleaved with EcoRI and BamHI to give an about 190 bp fragment.

Thereafter, as shown in FIG. 10, a large fragment obtained by cleaving the plasmid pGEMpβ-N with EcoRI and BamHI was ligated to the about 190 bp fragment obtained from above M13β-C (C2420pal), whereby an expression vector pGEMpβ was constructed. That is, the sequence integrated into this pGEMpβ so as to be expressed is as shown in SEQ ID NO: 1 in the Sequence Listing, where nucleotides 1 to 9 were derived from the vector.

Then, the pGEMpβ was transformed into *E. coli* JM109 (DE3) (Promega). The resulting transformant was cultured at 37° C. under shaking in a suitable medium containing isopropyl-β-D-thiogalactopyranoside until a D3 gene product was accumulated as a protein inclusion body in the microorganism.

The microorganism thus cultured was collected, disrupted by ultrasonication and centrifuged to recover the protein inclusion body. This protein inclusion body was washed and dissolved in 50 mM TRIS-HCl buffer, pH 8 containing 8M urea, 10 mM dithiothreitol, 50 mM NaCl and 5 mM ethylenediaminetetraacetic acid (EDTA) to give an about 10 mg/ml protein solution. This solution was named solubilized pD3-β.

To 1 part of the solubilized pD3-β were slowly added 100 parts of a solution containing reduced glutathione and oxidized glutathione (i.e. 50 mM potassium phosphate (pH 10.5) containing 1 mM reduced glutathione, 0.1 to 0.5 mM oxidized glutathione and 5 mM EDTA) but not containing any protein modifier.

The mixture was concentrated about 50-fold and the solvent was replaced by 5 mM potassium phosphate buffer (pH 10) containing 200 mM NaCl. This solution was named refolded pD3-β.

The specific activity of the resulting D3-β for decomposition of c30 was 15 U/mg. The measurement of this activity was described in detail in Japanese Patent laid-open Publication No. 264/1996.

pGEMpβ was transformed into *E. coli* JM109; and this transformant was deposited Jul. 3, 1995 with the National Institute of Bioscience and Human-Technology, Agency of Industrial Science and Technology, Japan (accession number: FERM BP-5793).

Hereinafter, an activity detection method, preparation method etc. are described for leucine aminopeptidase derived from germinated soybean cotyledons, which was used in combination to decompose soybean protein.

Example 12
Activity Detection for Leucine Aminopeptidase

The substrate used was leucine paranitroanilide, and the paranitroanilide released by the action of this enzyme was determined. Unless otherwise specified, the following conditions and method were used.

0.05 ml enzyme solution, 0.02 ml of 2 mM L-leucine paranitroanilide, 0.02 ml of 100 mM HEPES buffer (pH 7.0) and 0.11 ml H$_2$O were mixed and reacted at 37° C. for 20 minutes. The reaction was stopped by adding 0.05 ml of 50% aqueous acetic acid, and the amount of paranitroaniline released in the reaction solution was determined. The enzyme activity causing release of 1 μmole paranitroaniline per minute from leucine paranitroanilide as the substrate was assumed to be 1 Unit.

Example 13
Search for Leucine Aminopeptidase

The above detection method was used to search for decomposition activity in an extract of germinated soybean cotyledons. First, cotyledons 7 days after germination were examined for leucine paranitroanilide decomposition activity.

To cotyledons 7 days after seeding, 4 g (8 cotyledons), was added a 5-fold excess volume (20 ml) of an ice-cold buffer (20 mM potassium phosphate buffer pH 7.0, 200 mM NaCl, 10 mM 2-mercaptoethanol, 2 mM NaN$_3$), and the cotyledons were disrupted with a homogenizer, extracted, and filtered through a gauze. The filtrate was filtered at 32,000 g for 30 minutes at 4° C. The supernatant was filtered through a filter paper to give a crude extract. In this crude extract, the enzyme activity was present.

Example 14
Purification of Daidzu (Soybean) Leucine Aminopeptidase

Because the leucine paranitroanilide (Leu-pNA) decomposition activity was present in the extract from cotyledons 7 days after germination, the enzyme with this activity was designated daizdu leucine aminopeptidase (DLAP), and the purification of DLAP fractions (DLAP1 and DLAP2) was carried out in the following manner.

1. Extraction

To 600 g cotyledons 7 days after seeding was added a 5-fold excess volume (3000 ml) of an ice-cold buffer (20 mM potassium phosphate buffer pH 7.0, 200 mM NaCl, 0.1 mM Pefabloc SC (4-(2-aminoethyl)-benzenesulfonyl fluoride HCl), 10 μM E-64, 10 mM 2-mercaptoethanol, 2 mM NaN$_3$), and the cotyledons were disrupted with a homogenizer, extracted and filtered through a gauze. The filtrate was centrifuged at 32,000 g for 30 minutes at 4° C. The supernatant was filtered through a filter paper (No. 514 A, available from Advantec Toyo K.K.). The crude extract obtained as the filtrate was concentrated in a membrane concentration unit (MINITAN, available from Millipore company).

2. Ammonium Sulfate Fractionation

The pH of the crude extract thus prepared was confirmed (adjusted to pH 7.0 with NaOH), and this solution was made 40% saturation with ammonium sulfate by adding ammonium sulfate (763 g/3150 ml). The solution was stirred at 4° C. for 6 hours and centrifuged at 32,000 g for 30 minutes at 4° C. to give a supernatant. The supernatant was made 65% of saturation with ammonium sulfate by further adding ammonium sulfate (564 g/3,400 ml). It was stirred at 4° overnight (15 hours) and then centrifuged at 32,000 g for 30 minutes at 4° C. to recover precipitates. The precipitates were dissolved in 120 ml buffer (50 mM potassium phosphate buffer pH 7.0, 100 mM NaCl, 2 mM NaN$_3$) and dialyzed repeatedly against a buffer (2L×5, 16 hours) at 7° C. After dialysis, the dialysate was centrifuged at 32,000 g for 20 minutes at 4° C. and then filtered thorough a 0.2 μm filter (NALGENE filterware) to be applied to anion exchange chromatography in the subsequent step.

3. Anion Exchange Chromatography

The sample obtained in 2 above was fractionated through HILOAD 26/10 Q SEPHAROSE HP in the FPLC system (Pharmacia) as follows. About 190 ml sample was divided due to a large volume into 8 aliquots and each aliquot was subjected to this ion-exchange chromatography. The column was previously equilibrated with the same buffer as used in the previous dialysis, and after application of the sample, the column was washed with a 5-fold column volume of the buffer. Just after application of the sample, the eluted fraction including the wash, about 2,000 ml in total, was concentrated to 55 ml in an ultracentrifugation unit (MINITAN, manufactured by Millipore). This fraction was designated DLAP 1 fraction. This sample was adjusted to 1M ammonium sulfate by adding 7.26 g ammonium sulfate. The solution was centrifuged at 32,000 g for 20 minutes at 4° C. to give a supernatant to be applied to hydrophobic chromatography in the subsequent step. After washing, the active fraction remaining on the column was eluted with a linear gradient of from 100 mM to 300 mM NaCl in a 8-fold column volume of the buffer. The active fraction adsorbed in the column in this step was designated DLAP2 fraction. The DLAP2 fraction was eluted with 200 to 300 mM NaCl in the buffer, and the eluent, about 410 ml in total, was concentrated to 46 ml in an ultrafiltration unit (MINITAN, Millipore). This sample was adjusted to 1M ammonium sulfate by adding 6.07 g ammonium sulfate. This solution was centrifuged at 32,000 g for 20 minutes at 4° C. to be applied to hydrophobic chromatography in the subsequent step.

4. Hydrophobic Chromatography

The samples DLAP1 and DLAP2 obtained in 3 above were further fractionated with HILOAD 26/10 PHENYL SEPHAROSE HP in the FPLC system as follows. DLAP1, about 60 ml, was divided into 2 aliquots and each aliquot was applied to the column. The column was previously equilibrated with a buffer (50 mM potassium phosphate buffer pH 7.0, 1M $(NH_4)_2SO_4$, 2 mM $NaN_3$), and after application of the sample, the column was washed with a 5-fold column volume of the same buffer. Then, the active component was fractionated by eluting it in a decreasing linear gradient of from 1M to 0M ammonium sulfate in the buffer. In this step, the active fraction was eluted with 0.4 to 0M sulfate ammonium. This eluate, 600 ml, was concentrated to 3.0 ml with MINITAN and CENTRIPREP 10 (Amicon) The condensate was centrifuged at 32,000 g for 10 minutes at 4° C. to give a supernatant to be subjected to gel filtration in the subsequent step. DLAP2, about 46 ml, was applied to the column. The column was previously equilibrated with a buffer (50 mM potassium phosphate buffer pH 7.0, 1M $(NH_4)_2SO_4$, 2 mM $NaN_3$), and after application of the sample, the column was washed with a 5-fold column volume of the same buffer. Then, the active component was fractionated by eluting it in a decreasing linear gradient of from 1M to 0M ammonium sulfate in the buffer. In this step, the active fraction was eluted with 0.4M to 0M sulfate ammonium. This eluate, 100 ml, was concentrated to 1.0 ml with MINITAN and CENTRIPREP 10 (Amicon). The condensate was centrifuged at 32,000 g for 10 minutes at 4° C. to give a supernatant to be subjected to gel filtration in the subsequent step.

5. Gel filtration chromatography

The DLAP 1 obtained in above 4 was fractionated by gel filtration in HILOAD 26/60 SUPERDEX 200pg in the FPLC system as follows. The sample was divided into 2 aliquots and each aliquot was applied to chromatography. The column was equilibrated with a buffer (50 mM potassium phosphate buffer pH 7.0, 100 mM NaCl, 2 mM $NaN_3$) prior to fractionation of the sample. The obtained active fraction was concentrated to give a DLAP1 preparation.

The DLAP2 obtained in 4 above was fractionated by gel filtration through the same column in the FPLC. The obtained active fraction was concentrated to give a DLAP2 preparation.

An increase in specific activity by a series of the purification steps was determined. The specific activity of the above crude leucine aminopeptidase enzyme was about 5 U/mg, while the specific activity of the purified enzyme DLAP1 was about 160 U/mg, indicating that DLAP1 was purified about 32-fold in terms of specific activity in the purification process. Because the specific activity of the purified DLAP2 was also about 160 U/mg, DLAP2 was purified 32-fold in terms of specific activity. DLAP1 was detected more sensitively with alanine paranitroanilide (Ala-pNA) than Leu-pNA; that is, its specific activity was 270 U/mg in terms of activity unit using alanine paranitroanilide (Ala-pNA).

Hereinafter, the activity of DLAP1 will be expressed in activity measurements using alanine paranitroanilide. DLAP2 was detected more sensitively by use of phenylalanine paranitroanilide (Phe-pNA) than Leu-pNA; that is, its specific activity was 3200 U/mg in terms of activity unit using phenylalanine paranitroanilide(Phe-pNA).

Hereinafter, the activity of DLAP2 will be expressed in activity measurements using phenylalanine paranitroanilide.

From the activity staining of the enzyme in native PAGE, the molecular weight of active DLAP1 enzyme was estimated to be about 60 to 70 kD (see FIG. 12). From similar staining, the molecular weight of active DLAP2 enzyme was estimated to be about 45 to 55 kD (see FIG. 13). Hereinafter, the activity staining method is described.

Example 15

Activity Staining of DLAP1 and DLAP2 in Native PAGE 20, 60 and 120 mU enzyme was prepared in a Davis' sample preparation buffer (0.0625M TRIS-HCl buffer pH 6.8, 15% glycerol, 0.001% bromophenol blue) and electrophoresed in a commercial gel (MULTIGEL 2/15, Dai-Ichi Kagaku Yakuhin K.K.) in an electrophoresis buffer (3 g TRIS, 14.4 g/l glycine) at 5° C. To detect DLAP1, the gel after electrophoresis was incubated in solution A (50 mM potassium phosphate buffer pH 8.0, 0.5 mg/ml alanine-β-naphtylamide) in an incubator at 37° C. for 30 minutes. After washing with distilled water, the gel was stained with solution B (50 mM potassium phosphate buffer pH 8.0, 1 mg/l FAST BLUE B SALT (o-dianisidine, tetrazotized). FAST BLUE B SALT was supplied from Sigma, and all the other reagents from Nakarai Tesque K.K. From the result, the molecular weight of active DLAP1 enzyme was estimated to be about 60 to 70 kD (see FIG. 12).

DLAP2 was similarly detected using 50 m M potassium buffer pH 8.0 and 0.5 mg/ml phenylalanine-β-naphthylamide as solution A. From the result, the molecular weight of active DLAP2 enzyme was estimated to be about 45 to 55 kD (see FIG. 13).

The enzymatic properties of DLAP1 obtained in this manner are described below. The activity of DLAP1 was determined using L-alanine paranitroanilide as the substrate in place of L-leucine paranitroaniline used in the method of Example 12.

Example 16

Determination of Optimum pH and Optimum Temperature of DLAP 1

A change in enzyme activity due to reaction pH (optimum pH) was determined in the following manner.

The enzyme reaction buffers used were sodium citrate buffer (pH 3.0, 3.5, 4.0, 4.5, 5.0, 5.5, 6.0), MES buffer (pH 5.5, 6.0, 6.5, 7.0), HEPES buffer (pH 7.0, 7.5, 8.0), TRIS-HCl buffer (pH 8.0, 8.5, 9.0), and sodium carbonate buffer (pH 9.0, 9.5, 10.0, 10.5).

180 μl of 0.7 U DLAP1 was prepared in 50 mM buffer at each pH and pre-incubated for 5 minutes at 30° C. 20 μl of the substrate L-alanine paranitroanilide (0.4 mM for reaction) was added to each sample, then stirred and incubated for 20 minutes. 50 μl of 1 M sodium acetate buffer (pH 4.0) was added to stop the reaction.

Figure 14:
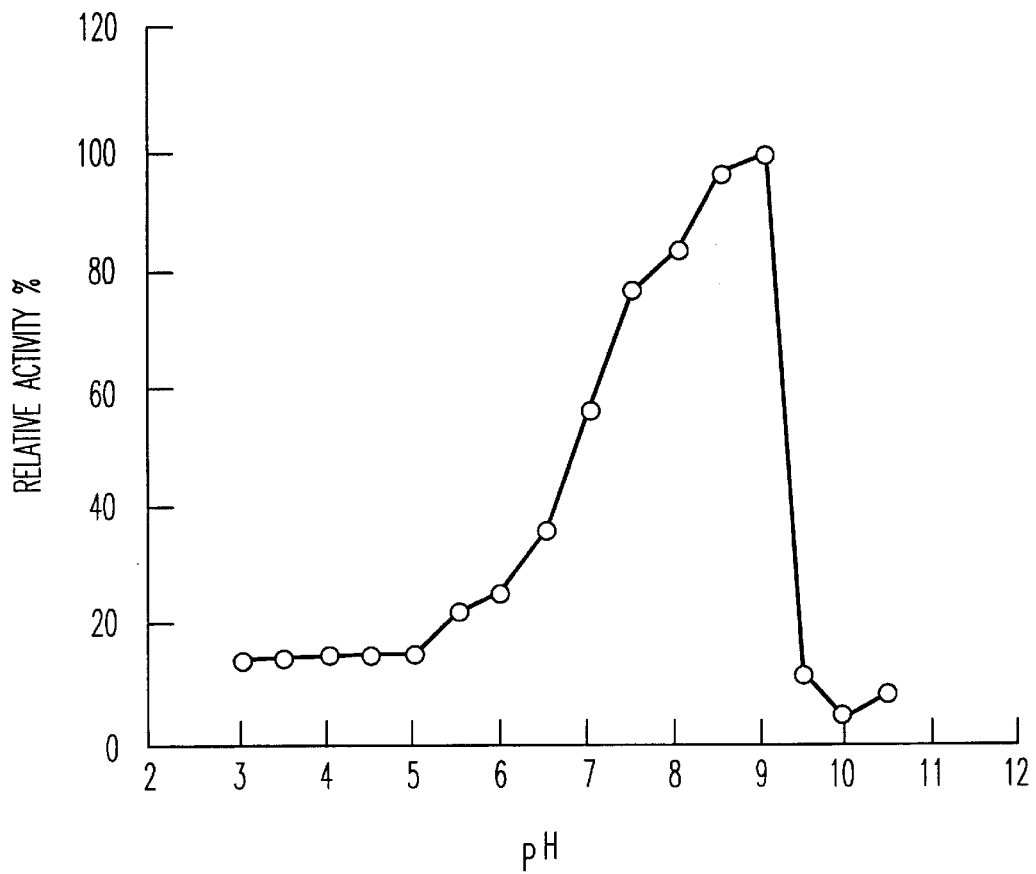
FIG. 14 shows a pH profile of the activity of aminopeptidase DLAP 1 activity at different pH values.

The measurement results are shown in FIG. 14. As can be seen from this graph, the optimum pH of DLAP1 of the present invention is in the range of about 5.5 to 9.5, preferably about 7 to about 9 (see FIG. 14).

A change in enzyme activity due to reaction temperature (optimum temperature) was determined as follows:

20 μl of the substrate L-alanine paranitroanilide (0.4 mM for reaction) was added to 50 mM MES buffer (pH 6.0) and 180 μl of thus obtained reaction solution was pre-incubated for 5 minutes at each temperature (25°, 30°, 37°, 42°, 50°, 60°, 70° C.). 0.7 U DLAP1 was further added to it.

This sample was stirred and then incubated for 20 minutes. 50 μl of 1M sodium acetate buffer (pH 4.0) was added to it to stop the reaction.

Figure 15:
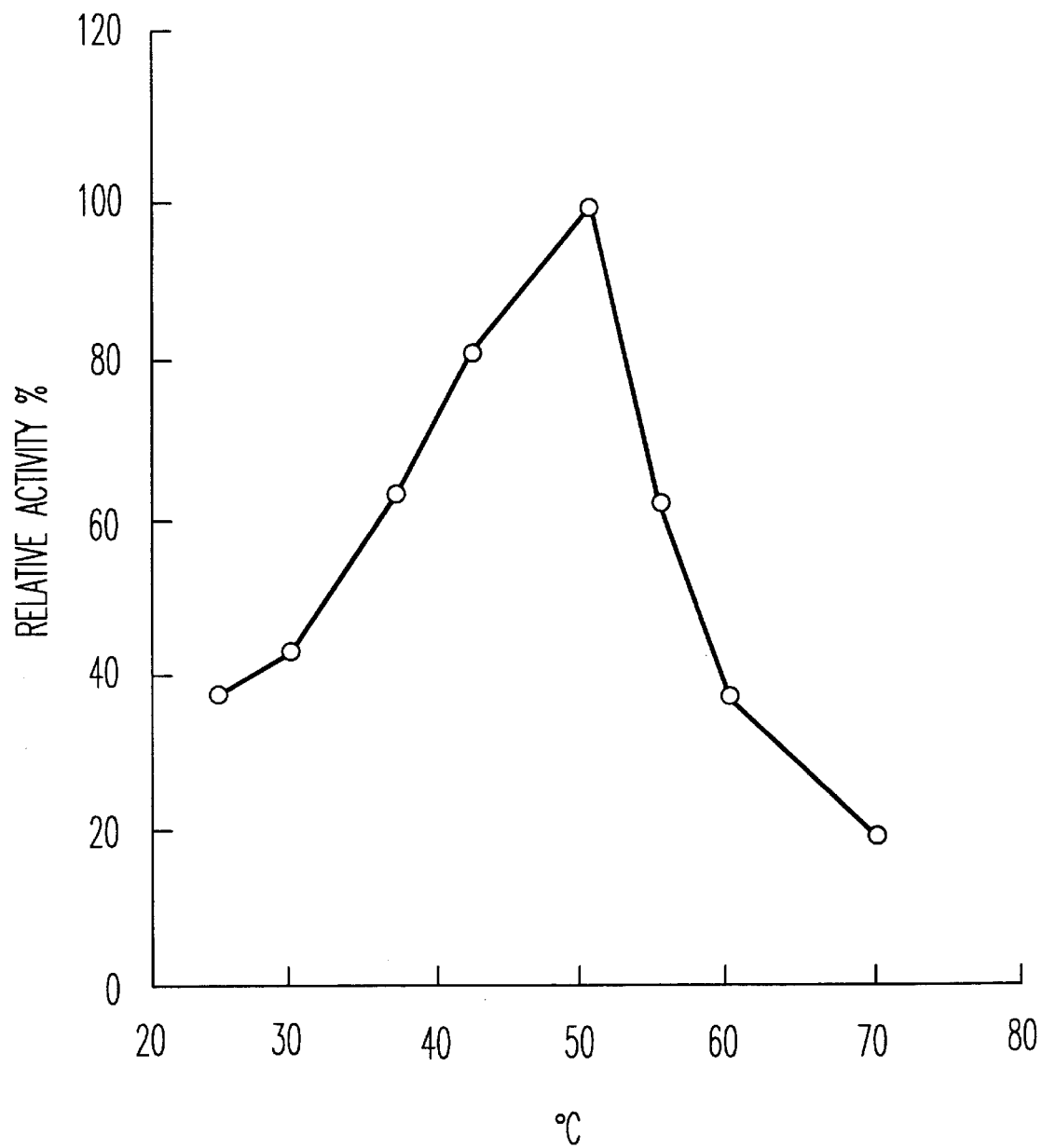
FIG. 15 shows a profile of aminopeptidase DLAP1 activity at different temperatures.

The measurement results are shown in FIG. 15. As can be seen from this graph, the optimum temperature of the DLAP 1 of the present invention is in the range of about 25 to 60° C., preferably about 35° to 55° C. (see FIG. 15).

The determination of temperature stability was carried out as follows:

900 U/ml enzyme was incubated in a buffer (pH 6.5) at predetermined temperatures (30°, 42°, 50°, 60° C.) for predetermined times (10, 20, 40, 60 minutes) and then examined for its remaining activity at 30° C.

Figure 16:
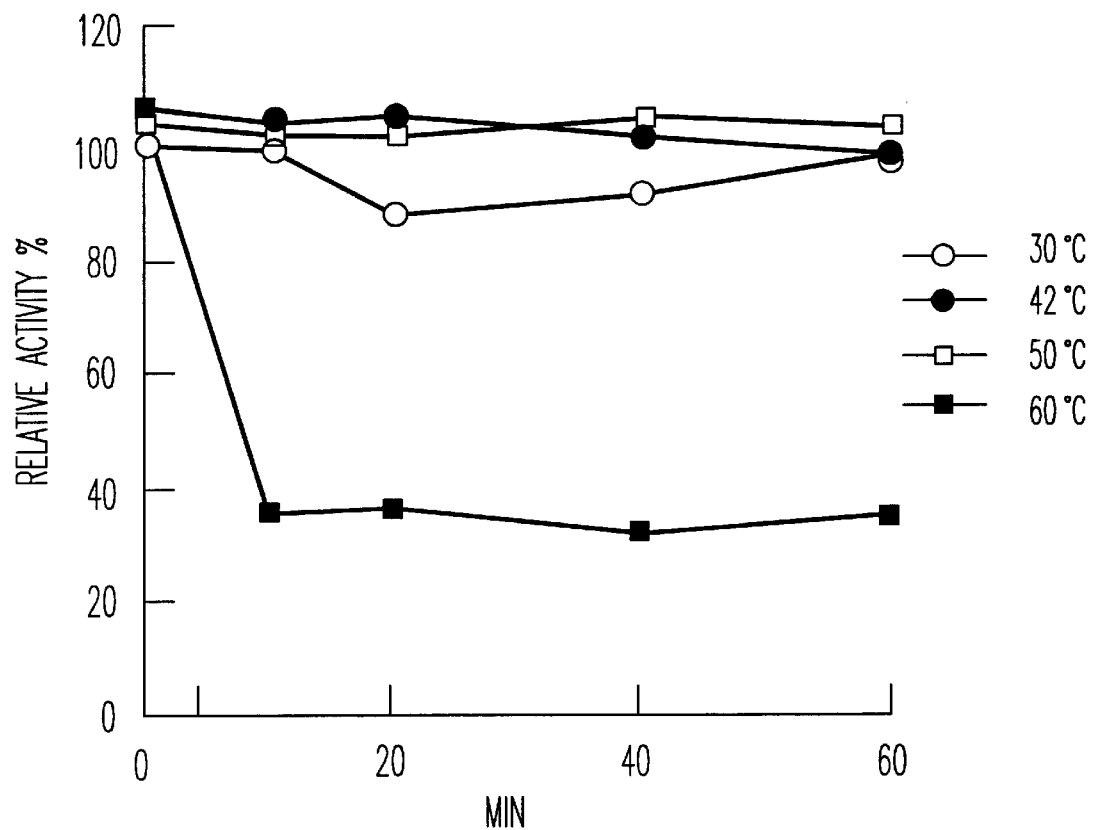
FIG. 16 shows a profile of the stability of aminopeptidase DLAP 1 activity at different temperatures.

The measurement results are shown in FIG. 16. The DLAP1 of the present invention maintained about 90% or more of the original activity even after 60-minute incubation at 50° C. and the activity was maintained about 25% or more after 10-minute incubation at 60° C. Therefore, the reaction temperature for longer reaction is preferably 50° C. or less.

Example 17
Effect of Protease Inhibitors on DLAP 1

The effect of protease inhibitors on the DLAP1 of the present invention was examined. The inhibitors used were actinonin, amastatin, antipain, alphamenine A, diprotin A, leuhistin, phenylmethane sulfonyl fluoride (PMSF), trans-epoxysuccinyl-L-leucylamide (4-guanidino)-butane (E-64), iodoacetamide, 1,10-orthophenanthroline, and N-ethylmaleimide (NEM). The 1,10-orthophenanthroline and N-ethylmaleimide were purchased from Nakarai Tesque K.K. and all the other inhibitors were purchased from Peptide Kenkyusho K.K.

In the presence of each inhibitor, the enzyme was left at room temperature (25° C.) for 20 minutes, and the remaining activity of the enzyme was determined in the same manner as in Example 12.

The results of activity measurements in the presence of each inhibitor are shown in Table 4. The enzyme was strongly inhibited by aminopeptidase inhibitors such as actinonin or amastatin.

TABLE 4

Effect of Each Protease Inhibitor on DLAP1

| Inhibitor | Concentration | Remaining Activity (Relative Value %) |
|---|---|---|
| — | — | 100 |
| actinonin | 100 μM | 48 |
| amastatin | 100 μM | 30 |
| antipain | 100 μM | 100 |
| alphamenine A | 100 μM | 100 |
| diprotin A | 100 μM | 100 |
| E-64 | 10 μM | 80 |
| leuhistin | 100 μM | 83 |
| PMSF | 10 mM | 100 |
| NEM | 100 mM | 95 |
| iodoacetamide | 50 mM | 100 |
| orthophenanthroline | 10 μM | 100 |

Example 18
Substrate Specificity of DLAP1 for Amino Acid Paranitroanilide Derivatives To examine the substrate specificity of DLAP1, the substrate specificity for each amino acid paranitroanilide derivative was compared with that for alanine paranitroanilide (Leu-pNA).

0.025 ml of 2 mM each amino acid paranitroanilide, 0.01 ml of 500 mM HEPES buffer (pH 8.0), and 0.04 ml H$_2$O were mixed, then pre-incubated for 5 minutes and reacted with 0.025 ml enzyme solution at 37° C. for 20 minutes. The reaction was stopped by adding 0.025 ml of 50% aqueous acetic acid, and the amount of paranitroaniline released in the reaction solution was determined. The enzyme activity causing release of 1 μmole paranitroaniline per minute from each amino acid paranitroanilide derivative was assumed to be 1 Unit. The decomposition activity for each substrate, relative to that for alanine paranitroanilide, is shown in Table 5.

TABLE 5

| Dipeptide | Relative Decomposition Activity |
|---|---|
| Ala-pNA | 100 |
| Gly-pNA | 97 |
| Leu-pNA | 65 |
| Ile-pNA | 21 |
| Val-pNA | 23 |
| Phe-pNA | 53 |
| Glu-pNA | 15 |
| Asp-pNA | 10 |
| Lys-pNA | 93 |
| Arg-pNA | 78 |
| His-pNA | 12 |
| Met-pNA | 103 |
| <Glu-pNA | 9 |
| Pro-pNA | 18 |

The enzymatic properties of DLAP2 obtained in Example 14 in the same manner as DLAP 1 are described below. The enzyme activity of DLAP2 was determined by use of L-phenylalanine paranitroanilide in place of the substrate L-leucine paranitroanilide in the method of Example 12.

Example 19
Determination of Optimum pH and Optimum Temperature of DLAP2

A change in enzyme activity due to reaction pH (optimum pH) was determined in the following manner.

The enzyme reaction buffers used were sodium citrate buffer (pH 3.5, 4.0, 4.5, 5.0, 5.5, 6.0), MES buffer (pH 5.5, 6.0, 6.5, 7.0), HEPES buffer (pH 7.0, 7.5, 8.0), TRIS-HCl buffer (pH 8.0, 8.5, 9.0), and sodium carbonate buffer (pH 9.0, 9.5, 10.0, 10.5).

180 μl of 0.7 U DLAP2 was prepared in 50 mM buffer at each pH and pre-incubated for 5 minutes at 30° C. 20 μl of the substrate L-phenylalanine paranitroanilide (0.4 mM for reaction) was added to each sample. It was stirred and then incubated for 20 minutes. 50 μl of 1M sodium acetate buffer (pH 4.0) was added to stop the reaction.

Figure 17:
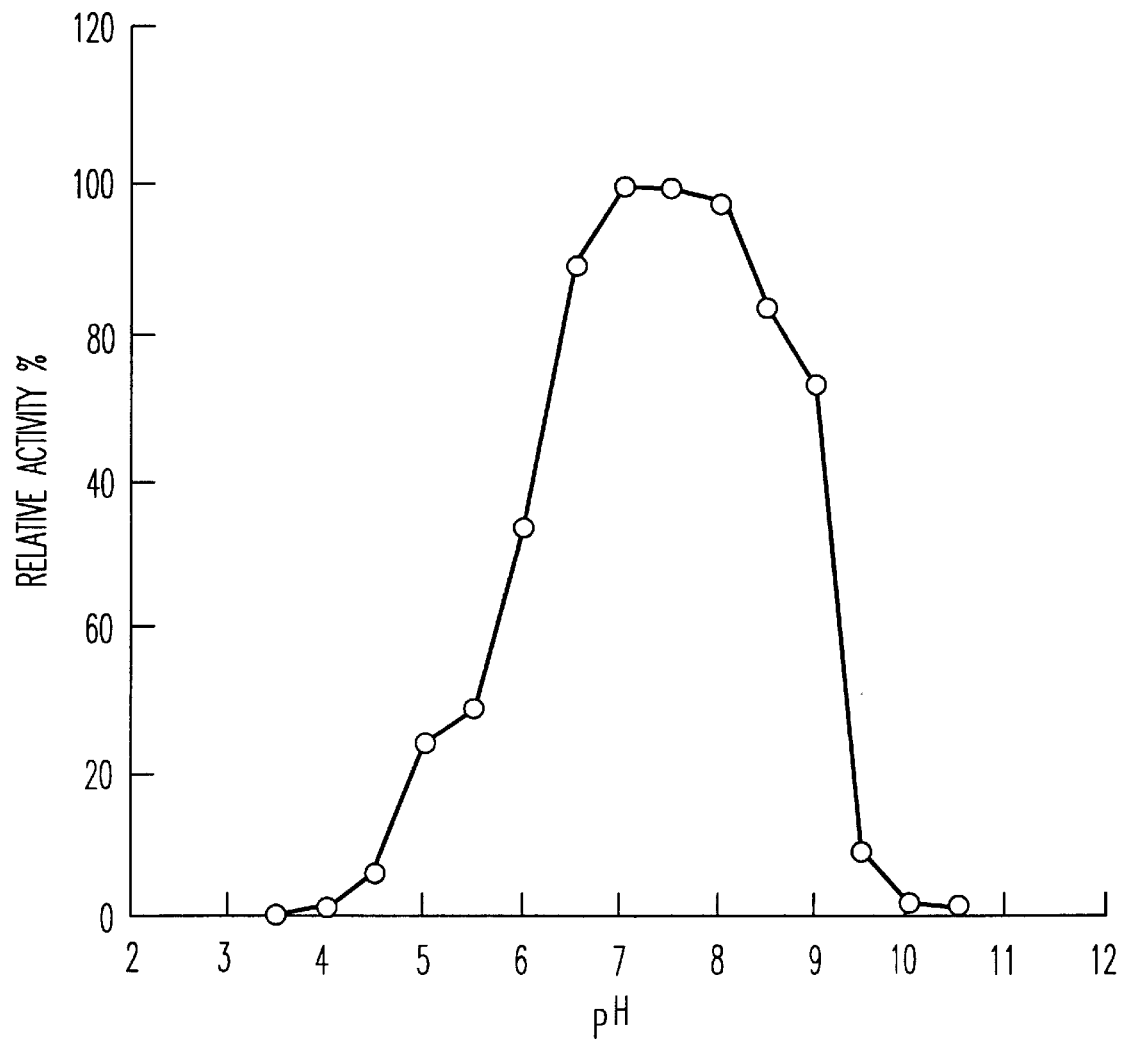
FIG. 17 shows a pH profile of aminopeptidase DLAP2 activity at different pH values.

The measurement results are shown in FIG. 17. As can be seen from this graph, the optimum pH of DLAP2 of the present invention is in the range of about 5.0 to 9.0, preferably about 6 to about 9 (see FIG. 17).

A change in enzyme activity due to reaction temperature (optimum temperature) was determined as follows:

20 μl of the substrate L-phenylalanine paranitroanilide (0.4 mM for reaction) was added to 50 mM MES buffer (pH 6.0) and 180 μl of thus obtained solution was pre-incubated for 5 minutes at each temperature (25°, 30°, 37°, 42°, 50°, 60°, 70° C.). 0.7 U DLAP2 was further added to it. The sample was stirred and then incubated for 20 minutes. 50 μl of 1M sodium acetate buffer (pH 4.0) was added to stop the reaction.

Figure 18:
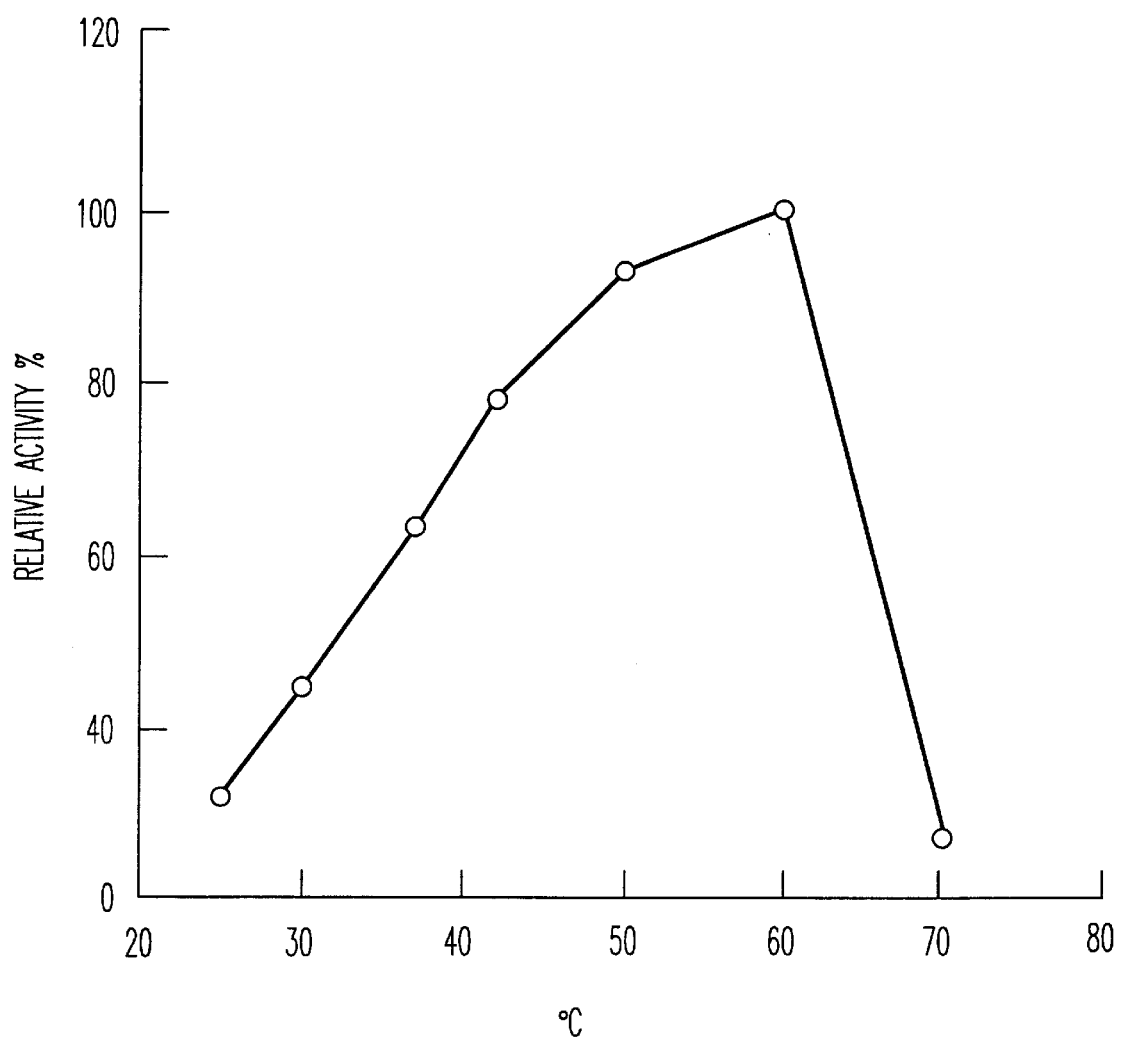
FIG. 18 shows a profile of aminopeptidase DLAP2 activity at different temperatures.

The measurement results are shown in FIG. 18. As can be seen from this graph, the optimum temperature of the DLAP2 of the present invention is in the range of about 30° to 70° C., preferably about 35° to 65° C. (see FIG. 18).

Example 20.
Effect of Protease Inhibitors on DLAP2

The effect of inhibitors on the DLAP2 of the present invention was examined. The inhibitors used were actinonin, amastatin, antipain, alphamenine A, diprotin A, leuhistin, phenylmethane sulfonyl fluoride (PMSF), trans-epoxysuccinyl-L-leucylamide (4-guanidino)-butane (E-64), 1,10-orthophenanthroline, N-ethylmaleimide (NEM), and iodoacetamide. The 1,10-orthophenanthroline and N-ethylmaleimide were purchased from Nakarai Tesque K.K. and all the other inhibitors from Peptide Kenkyusho K.K.

In the presence of each inhibitor, the enzyme was left at room temperature (25° C.) for 20 minutes, and the remaining activity of the enzyme was determined in the same manner as in Example 12.

The results of activity measurements in the presence of each inhibitor are shown in Table 6. The enzyme was strongly inhibited by actinonin of aminopeptidase inhibitors, and weakly inhibited by PMSF.

TABLE 6

Effect of Protease Inhibitors on DLAP2

| Inhibitor | Concentration | Remaining Activity (Relative Value %) |
|---|---|---|
| — | — | 100 |
| actinonin | 100 μM | 37 |
| amastatin | 100 μM | 86 |
| antipain | 100 μM | 100 |
| alphamenine A | 100 μM | 100 |
| diprotin A | 100 μM | 100 |
| E-64 | 10 μM | 98 |
| leuhistin | 100 μM | 100 |
| PMSF | 10 mM | 67 |
| NEM | 100 mM | 89 |
| iodoacetamide | 50 mM | 100 |
| orthophenanthroline | 10 μM | 75 |

Example 21
Substrate Specificity of DLAP2 for Amino Acid Paranitroanilide Derivatives To examine the substrate specificity of DLAP2, the substrate specificity for each amino acid paranitroanilide derivative was compared with that for phenylalanine paranitroanilide (Phe-pNA). 0.025 ml of 2 mM each amino acid paranitroanilide, 0.01 ml of 500 mM HEPES buffer (pH 8.0), and 0.04 ml $H_2O$ were mixed and then reacted with 0.025 ml enzyme solution at 37° C. for 20 minutes. The reaction was stopped by adding 0.025 ml of 50% aqueous acetic acid, and the amount of paranitroaniline released in the reaction solution was determined. The enzyme activity causing release of 1 μmole paranitroaniline per minute from each amino acid paranitroanilide derivative as the substrate was assumed to be 1 Unit. The decomposition activity for each substrate, relative to that for phenylalanine paranitroanilide, is shown in Table 7.

TABLE 7

| Synthetic Substrate | Relative Decomposition Activity (%) |
|---|---|
| Phe-pNA | 100 |
| Ala-pNA | 3 |
| Gly-pNA | 2 |
| Leu-pNA | 5 |
| Ile-pNA | 0 |
| Val-pNA | 0 |
| Glu-pNA | 0 |
| Asp-pNA | 0 |
| Lys-pNA | 0 |
| Arg-pNA | 0 |
| His-pNA | 0 |
| Met-pNA | 3 |
| <Glu-pNA | 0 |
| Pro-pNA | 3 |

Example 22
Decomposition of Soybean Protein with Aminopeptidase GX, D3, DLAP1, and DLAP2

A method of decomposing soybean protein with the above characterized aminopeptidase GX, D3, DLAP1 and DLAP2 prepared from germinated soybean cotyledons in the manner described above is described below.

1. Primary Decomposition of Soybean Protein with Protease D3

The soybean protein used was a soybean protein preparation, AJIPRON SU (Ajinomoto Co. Inc). An aqueous solution of AJIPRON SU (2.5 g/35 ml MILLI-Q water) was sterilized in an autoclave at 120° C. for 10 minutes and then adjusted to pH 4.0 with HCl. This substrate solution (2.5 g/40 ml) was reacted with the refolded pD3-β from the recombinant E. coli (FERM BP-5793) prepared in Example 11. For this reaction, 1 ml of the refolded pD3-β (25 U/ml), 0.4 ml of 5M aqueous sodium chloride and 0.5 ml of 20 mM aqueous cysteine were mixed with 8 ml of the above substrate solution and reacted at 37° C. for 0 to 72 hours. The progress of the decomposition was monitored by quantifying nitrogen in the form of amino and imino groups as described in Japanese Patent laid-open Publication No. 264/1996 with 4-nitro-7-nitorobenzo-2-oxa-1,3-diazole (NBD-F) reagent (K. Imai, and Y. Watanabe, Anal. Chim. Acta., 130, 377–383 (1983)). The results are shown in Table 8.

TABLE 8

| Reaction Time | NBD-F value (mM) |
|---|---|
| 0 hour | N.D. |
| 24 hours | 60 |

TABLE 8-continued

| Reaction Time | NBD-F value (mM) |
|---|---|
| 48 hours | 89 |
| 72 hours | 106 |

2. Secondary Decomposition of Soybean Protein with Aminopeptidase GX

The primary hydrolysate obtained after 72-reaction in 1 above was decomposed with GX prepared in Example 3. The primary hydrolysate obtained in 1 above was adjusted to about pH 7 with sodium hydroxide. 200 μl of 1 U GX was added to 200 μl of the primary hydrolysate (containing 10 mg substrate) and 400 μl of thus obtained solution was reacted at 42° C. for 72 hours (Group 1). 200 μl of 1 U GX was made 400 μl(not containing the substrate) and incubated at 42° C. for 72 hours (Control 1), and 200 μl of the primary hydrolysate (containing 10 mg substrate) obtained in 1 above was diluted to 400 μl and incubated at 42° C. for 72 hours (Control 2).

The amino acid analysis of the hydrolysates after 72-hour reaction was carried out. The results are shown in Table 9.

As shown in Table 9, both glutamic acid and aspartic acid in group 1 were released much more than other amino acids.

TABLE 9

Amino Acid Analysis in Each Group After 72 Hours (mM)

|  | Group 1 | Control 1 | Control 2 |
|---|---|---|---|
| aspartic acid | 2.6 | N.D. | 0.3 |
| asparagine | 1.5 | N.D. | 0.4 |
| glutamic acid | 5.4 | N.D. | 1.6 |
| glutamine | 0.8 | N.D. | 0.6 |
| threonine | 0.8 | N.D. | 0.5 |
| serine | 2.7 | N.D. | 0.6 |
| proline | 0 | N.D. | 0 |
| glycine | 1.7 | N.D. | 0.5 |
| alanine | 2.4 | N.D. | 0.8 |
| valine | 0.9 | N.D. | 0.9 |
| cystine | 2.0 | N.D. | 2.0 |
| methionine | 0.7 | N.D. | 0.7 |
| isoleucine | 1.4 | N.D. | 1.2 |
| leucine | 1.7 | N.D. | 1.5 |
| tyrosine | 0 | N.D. | 0 |
| phenylalanine | 0.6 | N.D. | 0.5 |
| tryptophan | 0 | N.D. | 0 |
| lysin | 1.0 | N.D. | 0.8 |
| histidine | 0.4 | N.D. | 0.3 |
| arginine | 1.1 | N.D. | 0.9 |
| ammo acids in total | 27.1 | N.D. | 13.9 |

3. Secondary Decomposition of Soybean Protein with GX, DLAP1 and DLAP2

The primary hydrolysate obtained after 72-hour reaction in 1. above was decomposed with aminopeptidase GX and DLAP1 and DLAP2 prepared in Example 14. The primary hydrolysate obtained in 1. above was adjusted to about pH 7 with sodium hydroxide. 350 μl of a mixture of GX (1 U), DLAP 1 (320 U) and DLAP2 (100 U) was added to 50 μl of the primary hydrolysate (containing 2.5 mg substrate) and 400 μl of thus obtained solution was reacted at 42° C. for 0 to 72 hours (Group 2). Separately, 350 μl of a mixture of GX (1 U), DLAP1 (320 U) and DLAP2 (100 U) was made 400 μl and incubated at 42° C. for 0 to 72 hours (Control 3). Only 50 μl of the primary hydrolysate (containing 2.5 mg substrate) obtained in 1 above was diluted to 400 μl and incubated at 42° C. for 0 to 72 hours (Control 4). The hydrolysate after 72-hour reaction in Group 2 was further hydrolyzed with constant-boiling HCl (Wako Pure Chemical Industries) in a vacuum ampule at 110° C. for 24 hours. The progress of the decomposition was monitored using NBD-F in the same manner as in above 1. The results are shown in Table 10.

TABLE 10

| | NBD-F value (mM) | | |
|---|---|---|---|
| Reaction Time | Group 2 | Control 3 | Control 4 |
| 0 hour | 13 | 8 | 26 |
| 24 hours | 35 | 9 | 25 |
| 48 hours | 39 | 9 | 27 |
| 72 hours | 38 | 9 | 25 |

The amino acid analysis of the hydrolysates after 72-hour reaction was carried out. The amino acid contents in the acid hydrolysate of Group 2 was expressed relative to those in the secondary hydrolysate of Group 2 (Table 11).

TABLE 11

Amino Acid Analysis in Each Group After 72-Hour Reaction (mM)

|  | Group 2 | Acid Hydrolysate of Group 2 | Group 3 | Group 4 |
|---|---|---|---|---|
| aspartic acid | 1.3 | 3.9 | 0.1 | 0.2 |
| asparagine | 1.4 | 0 | 0 | 0.2 |
| glutamic acid | 2.5 | 6.2 | 0.2 | 0.8 |
| glutamine | 1.5 | 0 | 0 | 0.3 |
| threonine | 1.3 | 1.4 | 0.2 | 0.3 |
| serine | 2.4 | 2.3 | 0.1 | 0.3 |
| proline | 1.8 | 2.1 | 0.2 | 0 |
| glycine | 2.4 | 2.4 | 0.2 | 0.2 |
| alanine | 2.3 | 1.9 | 0.3 | 0.4 |
| valine | 2.1 | 1.6 | 0.3 | 0.3 |
| cystine | 0.7 | 0.6 | 0 | 1.0 |
| methionine | 0.6 | 0.4 | 0.4 | 0.4 |
| isoleucine | 1.7 | 1.4 | 0.3 | 0.6 |
| leucine | 3.0 | 2.5 | 0.5 | 0.7 |
| tyrosine | 0.9 | 0.9 | 0.1 | 0 |
| phenylalanine | 1.3 | 1.3 | 0.1 | 0.3 |
| tryptophan | 0 | 0 | 0 | 0 |
| lysine | 2.1 | 1.9 | 0.2 | 0.4 |
| histidine | 0.7 | 0.7 | 0.1 | 0.2 |
| arginine | 2.1 | 2.0 | 0.1 | 0.4 |
| amino acids in total | 32.1 | 33.5 | 3.4 | 7.0 |

As shown in Table 11, the total amino acids in the secondary hydrolysate of Group 2 are 32.1 mM and the total amino acids in the acid hydrolysate of Group 2 are 33.5 mM. In Group 2, the yield of the amino acids in the secondary hydrolysate Group 2 is therefore about 95.8% of the acid hydrolysate.

In group 2, the fact that other amino acids besides both aspartic acid and glutamic acid were highly released indicates the effect of both DLAP1 and DLAP2 in addition to that of aminopeptidase GX.

EFFECT OF THE INVENTION

The novel aminopeptidase GX of the present invention is an enzyme which is extremely useful in producing highly decomposed hydrolysates with high contents of acidic amino acids from starting materials containing peptides and proteins. That is, as shown in Example 8, the enzyme of the present invention releases acidic amino acids which are only slightly released with even aminopeptidase M having broad substrate specificity.

The novel aminopeptidase GX of the present invention can be used in combination with a conventional protein decomposition method, so that those substrates particularly having N-terminal acidic amino acid still not released by the conventional method can be decomposed. More specifically, with the aminopeptidase GX of the present invention, a peptide or protein containing glutamic acid or aspartic acid at the N-terminal end will release the glutamic acid or aspartic acid contributing to good taste. The peptide or protein hydrolysate thus obtained can be added to various materials such as foods, seasonings, feeds etc. Particularly, as shown in Example 22, protease D3, DLAP1 and DLAP2 which all were derived from germinated soybean cotyledons can be used in combination to decompose soybean protein and a combination of these enzymes results in about 95.8% yield based on a hydrochloric acid hydrolysate of soybean protein.

In addition, major components in soybean protein, e.g. β-conglisinin, glycine etc., are known to contain acidic amino acid-enriched sequences such as -Glu-Glu-Glu-Glu-Glu- etc. (J. J. Doyle et al., J. Biol. Chem., 261 9228 (1986), J. D. Ng et al., Plant Physiol., 101, 713 (1993), N. C. Nielsen et al., Plant Cell 1 313 (1989)), and these sequences would not be decomposed with a conventional protease or peptidase. The aminopeptidase GX of the present invention derived from germinated soybean cotyledons is considered to have best specificity and properties as an enzyme for efficiently decomposing acidic peptides derived from soybean protein. It is therefore believed that the enzyme of the present invention, aminopeptidase GX, is the most effective aminopeptidase for improving the release of acidic amino acids.

Although known aminopeptidases specific for acidic amino acids include those derived from porcine digestive tract membrane (A. Benajiba et al., Eur. J. Biochem. 107, 381 (1980)) and from lactic acid bacteria (F. A. Exterkate et al., Appln. Environ. Microbiol., 53, 577 (1987)) as EC. 3.4.11.7 glutamylaminopeptidase, the aminopeptidase GX of the present invention is not inhibited by an inhibitor (amastatin) of such a conventional aminopeptidase. Further, the aminopeptidase GX of the present invention is inhibited by leuhistine and actinonin, but no report has been made of glutamylaminopeptidase inhibited by said inhibitors. An aminopeptidase derived from yeast of the genus Rhodotolura (Japanese Patent laid-open Publication No. 244,381/1987) is also an acidic amino acid specific aminopeptidase, but this enzyme is different from the enzyme of the present invention because it is not inhibited by magnesium chloride or manganese chloride. Another aminopeptidase from soybean is also reported (Shinji Watanabe et al., Nippon Nogei Kagakkaishi 63(3), 617 (1988)), but this prior enzyme completely differs in substrate specificity from the aminopeptidase GX of the present invention Further, reported aminopeptidases derived from other plants do not include an enzyme similar to the enzyme of the present invention, and it can thus be concluded that the enzyme of the present invention is an acidic amino acid-specific aminopeptidase found for the first time and from a plant. Therefore, the novel aminopeptidase GX of the present invention is remarkable from a biological viewpoint as well.

Japanese priority application nos. 51848/1996 and 30458/1997 are incorporated herein by reference in their entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A purified aminopeptidase GX derived from germinated soybean cotyledon having the following properties:

a) optimum pH occurs in the range: about 5.5 to about 9.5;

b) optimum temperature occurs in the range: about 25° to about 60° C.;

c) temperature stability: about 80% or more activity remains after being kept at 50° C. for 80 minutes or about 40% or more activity remains after being kept at 60° C. for 40 minutes;

d) molecular weight: about 400 to 550 kD (gel filtration), about 380 to 460 kD (native PAGE), and three subunits of
       about 53 to 60 kD, about 30 to 32 kD, and about 25 to 28 kD (SDS-PAGE after reduction and heating);

e) substrate specificity: decomposes a peptide or protein containing glutamic acid or aspartic acid at the N-terminus to release the glutamic acid or aspartic acid;

f) inhibitors: inhibited by leuhistin, actinonin, alphamenine A or 1,10-orthophenanthroline; and g) effect of metal ions: inhibited by magnesium or copper.

2. The aminopeptidase of claim 1, which is derived from a cell extract obtained by disrupting germinated soybean cotyledons.

3. A method of hydrolyzing a peptide or protein, which comprises contacting a peptide or protein with an effective amount of the aminopeptidase of claim 1.

4. The method of claim 3, wherein cysteine protease D3 derived from germinated soybean cotyledons or a crude enzyme solution containing the same is present during said contacting step.

5. The method of claim 4, wherein leucine aminopeptidase or a crude enzyme solution containing the same is present during said contacting step.

* * * * *